(12) United States Patent
Yu et al.

(10) Patent No.: US 11,867,699 B2
(45) Date of Patent: Jan. 9, 2024

(54) DETECTING AN ANALYTE

(71) Applicant: THE UNIVERSITY OF QUEENSLAND, St. Lucia (AU)

(72) Inventors: Chengzhong Yu, St. Lucia (AU); Meihua Yu, Chapel Hill (AU); Chang Lei, Sinnamon Park (AU); Mohammad Kalantari, Annerley Queensland (AU)

(73) Assignee: THE UNIVERSITY OF QUEENSLAND, St Lucia (AU)

( * ) Notice: Subject to any disclaimer, the term of this patent is extended or adjusted under 35 U.S.C. 154(b) by 681 days.

(21) Appl. No.: 16/308,219

(22) PCT Filed: Jun. 12, 2017

(86) PCT No.: PCT/AU2017/050584
§ 371 (c)(1),
(2) Date: Dec. 7, 2018

(87) PCT Pub. No.: WO2017/210754
PCT Pub. Date: Dec. 14, 2017

(65) Prior Publication Data
US 2019/0265247 A1    Aug. 29, 2019

(30) Foreign Application Priority Data
Jun. 10, 2016 (AU) ................................ 2016902275

(51) Int. Cl.
*G01N 33/58* (2006.01)
*C01B 33/113* (2006.01)
(Continued)

(52) U.S. Cl.
CPC .......... *G01N 33/588* (2013.01); *C01B 32/15* (2017.08); *C01B 33/113* (2013.01); *C01B 33/18* (2013.01);
(Continued)

(58) Field of Classification Search
CPC ................ G01N 33/588; G01N 21/64; G01N 33/54346; G01N 33/587; C01B 33/113; B82Y 15/00
(Continued)

(56) References Cited

U.S. PATENT DOCUMENTS

| 7,563,451 B2 * | 7/2009 | Lin ........................ A61K 9/143 424/400 |
| 2004/0101822 A1 | 5/2004 | Wiesner et al. |

(Continued)

FOREIGN PATENT DOCUMENTS

| CN | 1742094 A | 3/2006 |
| CN | 1984989 A | 6/2007 |

(Continued)

OTHER PUBLICATIONS

Chen et al., Geometrical confinement of quantum dots in porous nanobeads with ultraefficient fluorescence for cell-specific targeting and bioimaging, Apr. 2012, Royal Society of Chemistry, 9568-9575 (Year: 2012).*

(Continued)

*Primary Examiner* — Christopher L Chin
(74) *Attorney, Agent, or Firm* — Nixon & Vanderhye P.C.

(57) ABSTRACT

This invention provides a method for detecting an analyte in a sample, including a step of contacting said analyte with a nanoparticle to facilitate binding thereto, wherein the nanoparticle comprises: (i) a core; (ii) pores extending radially from said core and being defined by spaces between an array of dendritic spikes radiating outwardly from a surface of the core, wherein the pores have an average pore size of between about 10 nm and about 20 nm; (iii) a binding agent for binding the analyte; and (iv) a detection agent immobi- (Continued)

lized within said pores; to thereby detect said analyte. This invention also provides kits, compositions and products comprising said nanoparticle.

6 Claims, 8 Drawing Sheets

(51) Int. Cl.
| | |
|---|---|
| G01N 33/543 | (2006.01) |
| G01N 21/64 | (2006.01) |
| C01B 32/15 | (2017.01) |
| C01B 37/02 | (2006.01) |
| C01B 33/18 | (2006.01) |
| B82Y 15/00 | (2011.01) |
| B82Y 30/00 | (2011.01) |
| B82Y 40/00 | (2011.01) |

(52) U.S. Cl.
CPC ............ *C01B 33/185* (2013.01); *C01B 37/02* (2013.01); *G01N 21/64* (2013.01); *G01N 33/54346* (2013.01); *G01N 33/587* (2013.01); *B82Y 15/00* (2013.01); *B82Y 30/00* (2013.01); *B82Y 40/00* (2013.01); *C01P 2004/62* (2013.01); *C12Y 111/01007* (2013.01)

(58) Field of Classification Search
USPC ........ 436/524, 525, 527; 977/773, 774, 779, 977/780, 781
See application file for complete search history.

(56) References Cited

U.S. PATENT DOCUMENTS

| | | |
|---|---|---|
| 2006/0160064 A1 | 7/2006 | Carbonell |
| 2010/0137143 A1 | 6/2010 | Rothberg et al. |
| 2012/0021034 A1* | 1/2012 | Zink ............... B22F 1/054 977/773 |
| 2012/0164749 A1 | 6/2012 | Luchini et al. |
| 2014/0308756 A1 | 10/2014 | Gautier et al. |
| 2015/0031575 A1 | 1/2015 | Fu et al. |
| 2015/0076392 A1 | 3/2015 | Fu |
| 2015/0308956 A1 | 10/2015 | Burn et al. |
| 2016/0178636 A1 | 6/2016 | Maeji et al. |

FOREIGN PATENT DOCUMENTS

| | | |
|---|---|---|
| CN | 101048663 A | 10/2007 |
| CN | 101443048 A | 5/2009 |
| CN | 102507953 A | 6/2012 |
| CN | 102815742 A | 12/2012 |
| CN | 103403546 A | 11/2013 |
| CN | 103954751 A | 7/2014 |
| CN | 103988081 A | 8/2014 |
| CN | 104364188 A | 2/2015 |
| CN | 104553215 A | 4/2015 |
| CN | 104956206 A | 6/2015 |
| CN | 105452299 A | 3/2016 |
| WO | 03003015 A2 | 1/2003 |
| WO | 2005017525 A1 | 2/2005 |
| WO | 2008069258 A1 | 6/2008 |
| WO | 2015160317 A1 | 10/2015 |

OTHER PUBLICATIONS

Wang et al., Peroxidase-like activity of mesoporous silica encapsulated Pt nanoparticle and its application in colorimetric immunoassay, Dec. 2014, Analytica Chimica Acta, 53-63 (Year: 2014).*
Goel et al ("Engineering Intrinsically Zirconium-89 Radiolabeled Self-Destructing Mesoporous Silica Nanostructures for in Vivo Biodistribution and Tumor Targeting Studies", Adv. Sci. 2016, 3, 1600122, pp. 1-11) (Year: 2016).*
Du et al (Dendritic Silica Particles with Center-Radial Pore Channels: Promising Platforms for Catalysis and Biomedical Applications, Small, 2015, 11, No. 4, 392-413) (Year: 2015).*
International Search Report for PCT/AU2017/050584, dated Sep. 13, 2017, 8 pages.
Written Opinion of the ISA for PCT/AU2017/050584, dated Sep. 13, 2017, 11 pages.
Slowing, Igor I., et al., "Mesoporous silica nanoparticles for drug delivery and biosensing applications", Advanced Functional Materials, vol. 17, No. 8, 2007, pp. 1225-1236.
Knežević, Nikola Ž., et al., "Magnetic mesoporous silica-based core/shell nanoparticles for biomedical applications", Rsc Advances, vol. 3, No. 25, 2013, pp. 9584-9593.
Wang, Jin-Gui, et al., "Anionic surfactant-templated mesoporous silica (AMS) nano-spheres with radially oriented mesopores", Journal of colloid and interface science, vol. 323, No. 2, 2008, pp. 332-337.
Xu, Chun, et al., "Core-Cone Structured Monodispersed Mesoporous Silica Nanoparticles with Ultra-large Cavity for Protein Delivery" Small, vol. 11, No. 44, 2015, pp. 5949-5955.
Han, Mingyong, et al., "Quantum-dot-tagged microbeads for multiplexed optical coding of biomolecules", Nature biotechnology, vol. 19, No. 7, 2001, p. 631-635.
Chen, L., "Research of Cluster Enzyme Labels and Their Application in Chemiluminescence Immunoassay," Chinese Doctoral Dissertations & Master's Theses Full-text Databases (Master), Engineering Science and Technology I, Oct. 15, 2011.
Zhang, S., et al., "Facile Fabrication of Dendritic Mesooorous SiO2@CdTe@SiO2 Fluorescent Nanoparticles for Bioimaging" Partical, vol. 33, No. 52, pp. 261-270, Feb. 29, 2016.
Marta N. Sanz-Ortiz, et al., "Templated Growth of Surface Enhanced Raman Scattering-Active Branched Gold Nanoparticles within Radial Mesoporous Silica Shells", ACS Nano, vol. 9, No. 10, 2015, 10489-10497.
Doo-Sik Moon, et al. "Tunable Synthesis of Hierarchical Mesoporous Silica Nanoparticles with Radial Wrinkle Structure", Langmuir, vol. 28, No. 33, 2012, pp. 12341-12347.

* cited by examiner

DETECTING AN ANALYTE

This application is the U.S. national phase of International Application No. PCT/AU2017/050584 filed 12 Jun. 2017, which designated the U.S. and claims priority to AU Patent Application No. 2016902274 filed 10 Jun. 2016, and AU Patent Application No. 2016902275 filed 10 Jun. 2016, the entire contents of each of which are hereby incorporated by reference.

FIELD OF THE INVENTION

This invention relates to methods and kits for detecting an analyte. In particular, the invention relates to methods and kits for detecting an analyte by contacting said analyte with a nanoparticle, such as a silica nanoparticle. Additionally, the present invention relates to a composition comprising a nanoparticle and products including said composition. In particular, the invention relates to a composition including a quantum dot-containing nanoparticle and products, such as electronic displays, solar cells and LED lights, containing same.

BACKGROUND TO THE INVENTION

An immunoassay is a biochemical method for detecting the presence or concentration of a macromolecule or small molecule. In their simplest form, immunoassay methods function by conjugating a detectable tag or label with the analyte that is desired to be detected via an antigen or antibody that is attached to the tag or label. By using an antibody or antigen to facilitate the binding with the analyte, high specificity for the particular analyte can be achieved. Once the labelled antibody or antigen is bound to the analyte it may then be detected via a number of mechanisms. Detectable labels or tags vary in nature and may be detected directly or may produce a signal or species that is in turn detectable. Label/tag types include enzymes, radioactive isotopes, DNA reporters, fluorogenic reporters, electrochemiluminescent tags and other species.

Enzyme-linked immunosorbent assay (ELISA) is one of the major analytical methods in both laboratory and clinical analysis due to its high reliability and sensitivity.[1] It uses antibodies and colour change to identify analytes and measure the concentration. In conventional ELISA, an analyte is specifically captured by one 1$^{st}$ antibody and then binds to one 2$^{nd}$ antibody conjugated with one detection agent, such as the enzyme horseradish peroxidase (HRP), which eventually generates one unit of colour change with the addition of substrates (such as 3,3',5,5'-Tetramethylbenzidine, TMB), the intensity of which is used for quantification.[1] However, for the diagnosis of diseases in their early stages and the detection of biomarkers when present in only trace amounts, colour changes by such detection methods could be below the limit of detection (LOD). Therefore, improving the sensitivity of detection methods, such as ELISA, for the detection of analytes with ultralow concentrations below the LOD is of great importance to many applications.

Signal amplification holds the key for increasing the sensitivity of various detection methods. By way of example, a concerted effort in recent years has been made to amplify the ELISA signal. Among various strategies, the use of enzyme-loaded particles to increase the enzyme amount for signal enhancement has become a promising method. In previous studies, liposome[2], gold nanoparticles,[3,4] polymer[5,6] and silica nanoparticles[7,8] were employed as matrices for enzyme loading. By immobilizing enzyme in polymer coated silica, a 267-fold improvement of sensitivity was reported, which is greater than similar immunoassay systems using silica nanoparticles of similar sizes.[5]

Many of these strategies rely on particles that are engineered to accommodate multiple labels such as the horse radish peroxidase (HRP) enzyme used in ELISA assays or quantum dots, on a single particle. When these single particles are conjugated to an antibody or antigen, analyte docking therefore links the analyte to multiple label species, producing a stronger detectable signal and therefore lowering the limit of detection.

Some of these strategies use solid particles onto the surface of which are loaded a number of label species. Signal amplification is enhanced by increasing the size of the host particles as a larger particle surface area provides more area for label attachment. This strategy has significant limitations, however, since larger particles can introduce steric hindrance problems where the large size of the conjugates may reduce their ability to dock with a solid support for detection, thus reducing their detectability.

The use of enzyme-enriched nanoparticles in ELISA has advantages and potential disadvantages. While the increased concentration of enzyme is advantageous for signal amplification, the enzyme activity also plays an important role on the enhancement of ELISA, which is determined by both the intrinsic bioactivity of the immobilized enzymes and the colour reaction efficacy between the enzymes and substrate molecules.[9] Many efforts have been devoted to enhance the intrinsic activity of enzymes immobilized by various methods.[5,7] For example, physical adsorption[10,11] is used to load enzymes with little influence on their activities, but the loading capacity is relatively low and it may cause enzyme release during the test. Besides, chemical binding is employed for achieving stable enzyme immobilization while resulting in a slight reduction in enzyme activity.[5] However, the influence of nanoparticle structure on the enzyme-substrate reaction is rarely reported. The substrates need to diffuse into the enzyme-loaded particles to react and generate signal. In this regard, easy access of substrates into enzyme loaded nanoparticles is likely to be beneficial for increasing the detection sensitivity.

Mesoporous silica nanoparticles (MSN) have attracted great attention in protein/drug delivery due to their large surface area, high pore volume, tuneable pore size and adjustable surface chemistry.[12,13] Several MSNs have been used to immobilize enzyme through chemical binding for signal amplifying, but enzymes were loaded on the outer surface of particles due to the small pore size which limits the loading amount and results in partial loss of enzyme activity.[7,14] In some other studies, HRP was loaded with MSNs through physical adsorption and the increased loading amounts were observed with the enlarged pore sizes.[10,11] Despite these attempts, the resultant signal amplification has been quite modest.

In the case of label-based immunoassay methods that use fluorescent labels, an additional challenge can arise when using multi- or high density label approaches due to a quenching effect. Individual fluorescent labels whose spatial positioning on a nanoparticle or other host is not well controlled can be easily quenched by each other, resulting in an artificially low signal being produced.

Accordingly, there remains a need for improved methods of detecting analytes by using nanoparticles that significantly enhance the signal amplification thereof.

A quantum dot-enhanced liquid crystal display (LCD) uses quantum dots (QDs) to facilitate display of electronic information. In this regard, a monolayer of QDs is typically illuminated by light from a series of blue LEDs in order to produce high quality/brightness white light for an LCD panel that shows the picture. Broadly, the QD layer contains two types of QDs, one type emits red light while the other emits green light on illumination by blue light. Blue light for the LCD is then typically provided by the blue light from the LEDs that simply passes through the layer so that red, green and blue (RGB) are present together to produce white light.

One of the common issues with such displays is that only a monolayer of QDs can be used in conventional designs since if the QDs are packed too closely together they quench each other, causing emission of poor quality light to the LCD. Additionally, a monolayer of QDs is generally not very efficient at capturing the light from the blue light emitting diodes (LEDs) and so the LEDs have to subsequently output a relatively intense light in order to provide enough light to illuminate the LCD panel via the QD layer. This may, for example, generate excessive heat, increase the power consumption of the display and shorten the lifetime of the display.

This problem with QDs is particularly pertinent with respect to battery powered devices, such as mobile phones and laptop computers. In these devices, the display consumes a high proportion of the energy in the battery so a lower power consumption display could significantly extend battery life. A similar argument can be made for LED lights that use QDs.

Accordingly, there remains a need for improving the efficiency of such QD layers, by capturing a greater proportion of the light emitted by the LEDs and converting it into emitted light for the LCD so as to allow for lower power, more energy efficient and/or longer lifetime displays.

SUMMARY OF THE INVENTION

The present invention is directed to methods and kits for detecting an analyte. Additionally, the present invention is directed to a composition including a quantum dot-containing nanoparticle and products containing same.

In a first aspect, the invention provides a method for detecting an analyte in a sample, including the step of contacting said analyte with a nanoparticle to facilitate binding thereto, wherein the nanoparticle comprises:
 (i) a core;
 (ii) a pore extending radially from said core;
 (iii) a binding agent for binding the analyte; and
 (iv) a detection agent immobilized within said pore;
 to thereby detect said analyte.

Suitably, the method of the present aspect further includes the step of producing a reporter signal from the detection agent. In particular embodiments, the step of producing the reporter signal comprises contacting the detection agent with a substrate so as to facilitate the production of said reporter signal therefrom. In other embodiments, the step of producing the reporter signal comprises contacting the detection agent with electromagnetic radiation so as to facilitate the production of said reporter signal therefrom. In one embodiment, the method of the present aspect further includes the step of detecting the reporter signal.

In a second aspect, the invention provides a diagnostic kit comprising: (i) a nanoparticle for detecting an analyte, wherein the nanoparticle comprises:
 (i) a core;
 (ii) a pore extending radially from said core;
 (iii) a binding agent for binding the analyte;
 (iv) a detection agent immobilized within said pore; and
 (v) instructions for use.

In one embodiment, the nanoparticle of the first and second aspects is a metal or metalloid nanoparticle.

Suitably, the metal or metalloid nanoparticle is a metal or metalloid oxide nanoparticle.

In embodiments, the metal or metalloid of the nanoparticle is selected from the group consisting of zinc, zirconium, silica, titanium, tin, aluminium, cerium, copper, indium, magnesium, nickel and iron.

Such metals and metalloids may be found within the nanoparticle of the first and second aspects in any one or more of their known oxide forms.

Preferably, the nanoparticle of the first and second aspects is a silica nanoparticle.

With respect to the invention of the first and second aspects, the pore is suitably substantially conical or suitably composed of a porosity that exists between an array of dendritic spikes radiating out from the core of the particle.

Suitably, for the invention of the first and second aspects, the pore has an average pore size of between about 5 nm and about 50 nm. Preferably, the pore has an average pore size of between about 10 nm and about 20 nm.

In one embodiment of the invention of the first and second aspects, the nanoparticle has an average particle size of between about 50 nm and about 250 nm.

Regarding the invention of the aformentioned aspects, the binding agent is suitably an antibody or functional fragment thereof.

With respect to the invention of the first and second aspects, the detection agent suitably is or comprises a bioluminescent agent, a chemiluminescent agent and/or a fluorescent agent. In one embodiment, the detection agent is or comprises a quantum dot. In an alternative embodiment, the detection agent is or comprises horse radish peroxidase.

In a third aspect, the invention provides a method for generating a nanoparticle displaying an anchoring group including the steps of:
 (i) providing a metal or metalloid source;
 (ii) contacting the metal or metalloid source with a base and optionally a surfactant in a liquid environment;
 (iii) contacting the product of step (ii) with a compound displaying the anchoring group;
 to thereby generate the nanoparticle displaying an anchoring group.

Preferably, the nanoparticle is selected from those described for the first and second aspects and so the metal or metalloid source is selected accordingly.

In one embodiment, the metal or metalloid source is silica and the compound displaying the anchoring group is a silicate displaying the anchoring group.

In one embodiment, a delay period of at least 5 minutes is provided between steps (ii) and (iii) so as to allow for the silica nanoparticle to form to a certain extent before the anchoring group is introduced.

In one embodiment, the method further comprises the step of treating the nanoparticle displaying an anchoring group to remove remaining surfactant template.

The removal of the surfactant may be by acid treatment.

In embodiments, the anchoring group is selected from the group consisting of a thiol, an amine, a carboxyl group, a polyethylene glycol group, a carbon chain and any combination thereof.

Preferably, the anchoring group is a thiol and the silicate displaying the anchoring group is a thiol-containing alkoxysilane.

In one embodiment, the surfactant may be a quaternary ammonium surfactant.

When the source is a silica source, it may be any hydrolyzable silica source although alkyl orthosilicates are preferred including, by way of non-limiting example only, TEOS and TMOS.

In a fourth aspect, the invention provides a composition comprising a nanoparticle dispersed in and/or on a substrate, wherein the nanoparticle comprises:
(i) a core;
(ii) a pore extending radially from said core; and
(iii) a plurality of quantum dots immobilized within said pore.

Suitably, the nanoparticle is a metal or metalloid nanoparticle, such as a metal or metalloid oxide nanoparticle. In some embodiments, the metal or metalloid of the nanoparticle is selected from the group consisting of zinc, zirconium, silica, titanium, tin, aluminium, cerium, copper, indium, magnesium, nickel and iron. Such metals and metalloids may be found within the nanoparticle of present aspect in any one or more of their known oxide forms.

Preferably, the nanoparticle is a silica nanoparticle.

In one embodiment, the pore is suitably substantially conical or suitably composed of a porosity that exists between an array of dendritic spikes radiating out from the core of the particle.

Suitably, the pore has an average pore size of between about 5 nm and about 50 nm. Preferably, the pore has an average pore size of between about 10 nm and about 20 nm.

In one embodiment, the nanoparticle has an average particle size of between about 100 nm and about 250 nm.

Suitably, the plurality of quantum dots comprises a first group of quantum dots and a second group of quantum dots, the first and second groups of quantum dots adapted to absorb a first portion of a first light from the light source to emit respectively a second light of a second colour and a third light of a third colour and further configured to transmit a second portion of the first light. Preferably, the first group of quantum dots is adapted to emit red light and the second group of quantum dots is adapted to emit green light upon excitation by a blue light source.

In one embodiment, the composition is or comprises a film.

In one embodiment, the composition is sealed within a substantially transparent container.

Suitably, the substrate is substantially transparent.

The substrate is suitably selected from the group consisting of a polymer, a monomer, a resin, a binder, a glass, a metal oxide and combinations thereof.

In a fifth aspect, the invention provides a display device comprising:
(i) a light source;
(ii) a light emitting layer comprising the composition of the fourth aspect and optically coupled to the light source; and
(iii) a display for receiving, at least in part, light emitted from the light emitting layer.

Suitably, the light source is or comprises a blue light source.

Preferably, the light source is or comprises a blue LED.

In one embodiment, the display is or comprises a liquid crystal module.

In a sixth aspect, the invention provides a light emitting diode device comprising:
(i) a cathode;
(ii) an electron transport layer on the cathode;
(iii) a light emitting layer formed on the electron transport layer, wherein the light emitting layer comprises the composition of the fourth aspect;
(iv) a hole transport layer on the light emitting layer; and
(v) an anode formed on the hole transport layer.

In a seventh aspect, the invention provides a solar cell, comprising:
(i) an electron conductor layer; and
(ii) an electron emitting layer comprising the composition of the fourth aspect and coupled to the electron conductor layer.

In a eighth aspect, the invention provides a method for emitting light, said method including the steps of:
(i) providing a light emitting layer comprising the composition of any one of the fourth aspect; and
(ii) exciting the light emitting layer with electromagnetic radiation of a frequency that is capable of absorption by one or more of the quantum dots therein;
to thereby emit light.

In one embodiment, the method of this aspect further includes the step of receiving the emitted light by a display.

In a ninth aspect, the invention provides a method for emitting electrons, said method including the steps of:
(i) providing an electron emitting layer comprising the composition of any one of the fourth aspect; and
(ii) exciting the electron emitting layer with electromagnetic radiation of a frequency that is suitable for absorption by one or more of the quantum dots therein;
to thereby emit electrons.

In one embodiment, the method of this aspect further includes the step of receiving the emitted electrons by an electron conductor layer of a solar cell.

In a tenth aspect, the invention provides a method for generating a nanoparticle having a plurality of quantum dots immobilized thereon including the steps of:
(i) providing a metal or metalloid source;
(ii) contacting the metal or metalloid source with a base and optionally a surfactant in a liquid environment;
(iii) contacting the product of step (ii) with a compound displaying the anchoring group;
(iv) contacting the product of step (iii) with said quantum dots;
to thereby generate the nanoparticle having the plurality of quantum dots immobilized thereon.

In one embodiment, the metal or metalloid source is a source of silica and the compound displaying the anchoring group is a silicate displaying the anchoring group.

Suitably, the anchoring group is selected from the group consisting of a thiol, an amine, a carboxyl group, a polyethylene glycol group, a carbon chain and any combination thereof. Preferably, the anchoring group is a thiol and the silicate displaying the anchoring group is a thiol-containing alkoxysilane.

In one embodiment, the method of this aspect further includes the step of dispersing the product of step (iv) in and/or on a substrate.

As used herein, except where the context requires otherwise, the term "comprise" and variations of the term, such as "comprising", "comprises" and "comprised", are not intended to exclude further elements, components, integers or steps but may include one or more unstated further elements, components, integers or steps.

It will be appreciated that the indefinite articles "a" and "an" are not to be read as singular indefinite articles or as otherwise excluding more than one or more than a single subject to which the indefinite article refers. For example, "a" pore includes one pore, one or more pores and a plurality of pores.

DETAILED DESCRIPTION OF THE INVENTION

Figure 1:
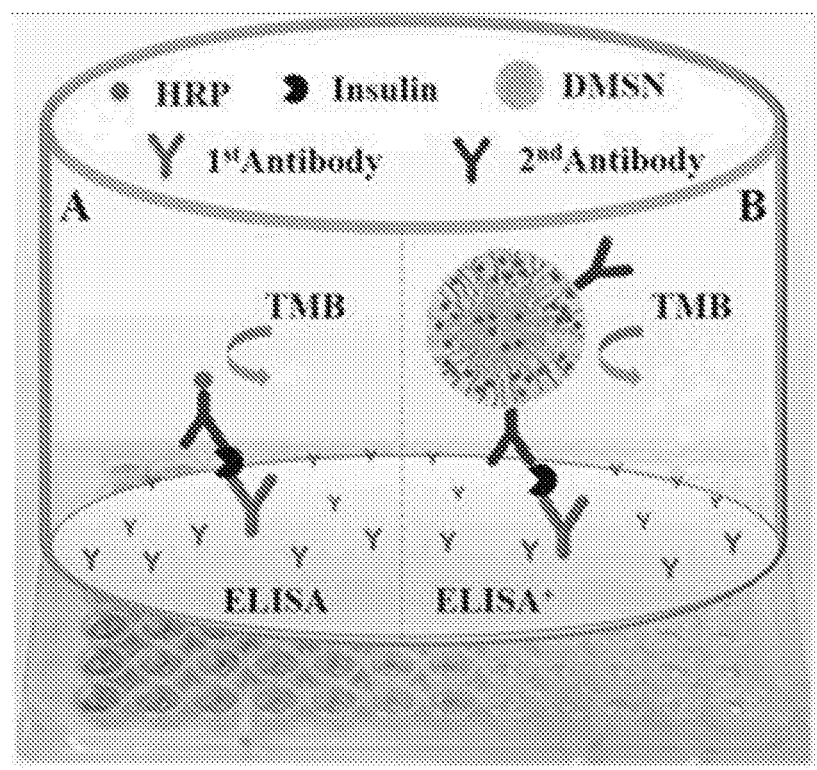
FIG. 1. Comparison between (A) traditional sandwich-like ELISA and (B) the ELISA using a designed mesoporous silica nanoparticle (DMSN) with high HRP loading and accessible dendritic channels to achieve the ultrasensitive detection.

The present invention is predicated, at least in part, on the surprising discovery that a specifically designed mesoporous silica nanoparticle with easily accessible radial pore channels resulted in significant signal amplification in analyte detection assays. Without being bound by any theory, it is proposed that the large and open radial channels allow for ultra-high detection agent loading and further provide an easily accessible space for substrate molecules to react with such detection agents, where such reactions are part of the analyte detection process. In other cases, where the detection agent is or comprises a fluorophore, the large and open pore structure likely facilitates easy loading of the fluorophores into the particle and appropriately unrestricted arrangement on the walls of the pores so as to minimize quenching.

Additionally, the present invention is at least partly predicated on the surprising discovery that a specifically designed mesoporous silica nanoparticle having quantum dots immobilized within easily accessible radial pore channels may result in significant signal amplification in products, such as electronic displays, LEDs and solar cells. Without being bound by any theory, it is proposed that the large and open pore structure likely facilitates easy loading of the quantum dots into the particle and appropriately unrestricted arrangement on the walls of the pores so as to minimize quenching.

Accordingly, in one aspect, the invention provides a method for detecting an analyte in a sample, including the step of contacting said analyte with a nanoparticle to facilitate binding thereto, wherein the nanoparticle comprises:
(i) a core;
(ii) a pore extending radially from said core;
(iii) a binding agent for binding the analyte; and
(iv) a detection agent immobilized within said pore;
to thereby detect said analyte.

As generally used herein, "analyte" refers to a molecule, typically a small molecule or a macromolecule, such as a polynucleotide or polypeptide, the presence, amount and/or identity of which are to be detected or determined. The analyte is recognized by a particular binding agent of the nanoparticle thereby forming an analyte/nanoparticle pair. Any analyte that may be detected using immunoassay methods may be detected using the method of the present invention.

In various embodiments, the analyte is or comprises, without limitation, a protein, a polypeptide, an antibody, an oligonucleotide, a polysaccharide, inorganic phosphate, ATP, GTP, UTP, CTP, ADP, GDP, cGMP, cAMP, CoA, FAD, FMN, FADP, NADH, NADPH, a thiol, glutathione, creatinine, creatine, hydrogen peroxide, a reactive oxygen species, or nitric oxide.

It will be appreciated that the term "nanoparticle" refers to particles that are submicron in size. The nanoparticles of the present invention may comprise any suitable material or composition that provides a rigid, stable particle for loading of the detection agent and is stable in the environment of the immunoassay, as are known in the art.

In one embodiment, the nanoparticle of the first and second aspects is a metal or metalloid nanoparticle, such as zinc, zirconium, silica, titanium, tin, aluminium, cerium, copper, indium, magnesium, nickel, iron and any combination thereof. Suitably, the metal or metalloid nanoparticle is a metal or metalloid oxide nanoparticle. Such metals and metalloids may be found within the nanoparticle of the invention in any one or more of their known oxide forms.

Exemplary compositions that may be used include, but are not limited to, silica oxides, such as silica dioxide, titanium oxides, such as titanium dioxide, aluminium oxides, such as alumina, indium tin oxide (ITO), fluorine-doped tin oxide (FTO), zirconium oxides, such as zirconia and cerium oxides, such as ceria, and combinations thereof.

In a preferred embodiment, the nanoparticle of the present invention is a silica nanoparticle. "Silica nanoparticle" refers to a nanoparticle comprising silica or silicon dioxide (i.e., $SiO_2$). This includes nanoparticles that are substantially, or entirely made up of silica, as well as those silica nanoparticles comprising other inorganic (e.g., a metal oxide) or organic components.

Suitably, the pore, such as one or a plurality of pores, of the nanoparticle is substantially conical or cone-shaped or substantially consists in a porosity that results from the spaces between an array of dendritic spikes radiating out from the core of the particle. In this regard, the skilled artisan will appreciate that a pore may be defined by the space between an array of dendritic spikes radiating out from the core.

It will be readily apparent that the term "conical" as used herein encompasses conical, frusto-conical or any other similar axi-symmetrical form. In other embodiments, the pore, including one or a plurality of pores, of the nanoparticle is substantially cylindrical. It will also be readily apparent that irregular or non-perfect forms of the aforementioned shapes are encompassed by the present invention.

In particular embodiments, the nanoparticles described herein are mesoporous nanoparticles. Mesoporous materials are typically defined as natural or synthetic materials having an average pore size or diameter of 2 nm to 50 nm (i.e., between those pore sizes that define micro- and macroporous materials).

Pore size may be measured by any means known in the art. Preferably, the pore size value is a composite or average of the individual pore sizes present throughout the nanoparticle of interest. This may be determined, for example, by a nitrogen sorption method and applying the Barrett-Joyner-Halenda (BJH) model, which is well known in the art.

Accordingly, the nanoparticle of the present invention may have an average pore size of between about 2 nm and about 50 nm, or any range therein such as, but not limited to, about 5 nm to about 40 nm, or about 10 nm to about 30 nm. In particular embodiments of the present invention, the nanoparticle has an average pore size of about 2 nm, 3 nm, 4 nm, 5 nm, 6 nm, 7 nm, 8 nm, 9 nm, 10 nm, 11 nm, 12 nm, 13 nm, 14 nm, 15 nm, 16 nm, 17 nm, 18 nm, 19 nm, 20 nm, 21 nm, 22 nm, 23 nm, 24 nm, 25 nm, 26 nm, 27 nm, 28 nm, 29 nm, 30 nm, 31 nm, 32 nm, 33 nm, 34 nm, 35 nm, 36 nm, 37 nm, 38 nm, 39 nm, 40 nm, 41 nm, 42 nm, 43 nm, 44 nm, 45 nm, 46 nm, 47 nm, 48 nm, 49 nm, 50 nm, or any range therein. In certain embodiments of the present invention, the nanoparticle has an average pore size of between about 5 nm and about 50 nm. In one preferred embodiment, the nanoparticle has an average pore size of between about 10 nm and about 20 nm.

With respect to the aforementioned pore size and shape of the nanoparticles described herein, it is presumed that such a design provides not only a significantly large surface area available for detection agent loading thereon, but also easy loading of detection agents into the porous structure and easily accessible pore channels for substrate molecules to react with such detection agents. Accordingly it is proposed that the significant signal amplification in analyte detection assays demonstrated herein is a function, at least in part, of such a pore design.

It will be appreciated by the skilled artisan that pore size, to some degree, may be determined by the particular detection agent to be immobilized therein. By way of example, larger detection agents and/or substrates will typically require a larger pore size. Additionally, a larger pore size may allow for easier access to the detection agent by a substrate thereof. Accordingly, the average pore size of the nanoparticle may vary with the particular detection agent (e.g., quantum dots, radioactive agents, horse radish peroxidase etc) to be immobilized therein.

Nanoparticles, including silica nanoparticles, have an average particle size, which refers to the average longest dimension of the particles, that may be, for example, no greater than 1000 nanometers, no greater than 500 nanometers, no greater than 200 nanometers, no greater than 100 nanometers, no greater than 75 nanometers, no greater than 50 nanometers, no greater than 40 nanometers, no greater than 25 nanometers, or no greater than 20 nanometers. The average particle size is often determined using transmission electron microscopy but various light scattering methods (e.g., laser diffraction) can be used as well. The average particle size typically refers to the average size of non-agglomerated and/or non-aggregated single nanoparticles.

The nanoparticle of the present invention may have an average particle size of between about 50 nm and about 800 nm, or any range therein such as, but not limited to, about 60 nm to about 400 nm, or about 80 nm to about 250 nm. In particular embodiments of the present invention, the nanoparticle has an average particle size of about 50 nm, 60 nm, 70 nm, 80 nm, 90 nm, 100 nm, 110 nm, 120 nm, 130 nm, 140 nm, 150 nm, 160 nm, 170 nm, 180 nm, 190 nm, 200 nm, 210 nm, 220 nm, 230 nm, 240 nm, 250 nm, 260 nm, 270 nm, 280 nm, 290 nm, 300 nm, 310 nm, 320 nm, 330 nm, 340 nm, 350 nm, 360 nm, 370 nm, 380 nm, 390 nm, 400 nm, 410 nm, 420 nm, 430 nm, 440 nm, 450 nm, 460 nm, 470 nm, 480 nm, 490 nm, 500 nm, 510 nm, 520 nm, 530 nm, 540 nm, 550 nm, 560 nm, 570 nm, 580 nm, 590 nm, 600 nm, 610 nm, 620 nm, 630 nm, 640 nm, 650 nm, 660 nm, 670 nm, 680 nm, 690 nm, 700 nm, 710 nm, 720 nm, 730 nm, 740 nm, 750 nm, 760 nm, 770 nm, 780 nm, 790 nm, 800 nm, or any range therein. In certain embodiments of the present invention, the nanoparticle has an average particle size of between about 50 nm and about 250 nm.

With respect to particle size, it would be appreciated by the skilled artisan that when designing a nanoparticle for a particular application, there exists a need to find a delicate balance between the appropriate size of loading surfaces to maximize the amount of detection agent loaded thereon (i.e., an increase of the particle size and/or pore size) and a small enough particle volume so as to remain suspended in solution and form analyte-nanoparticle complexes with acceptable diffusion kinetics (i.e., a decrease of the particle size). Accordingly, the average particle size of the nanoparticle may vary with the particular application (e.g., ELISA, immunofluorescence etc) for which it is to be used.

The nanoparticles of the present invention suitably demonstrate a high degree of monodispersity (i.e., a substantially uniform particle size) in order that a consistent strength of signal is generated on detection of a given quantity of analyte. In order to ensure reliable and consistent detection, it is advantageous to have a tight distribution of particle sizes, and consequently a high degree of uniformity in the number of detection agent species present on each nanoparticle to produce a uniform signal intensity.

Suitably, the polydispersity index (PDI) of the nanoparticles of the present invention as measured by dynamic light scattering (DLS) is less than or equal to about 0.2. In particular embodiments of the present invention, the polydispersity index (PDI) of the nanoparticles of the present invention as measured by dynamic light scattering (DLS) is about 0.01, 0.02, 0.03, 0.04, 0.05, 0.06, 0.07, 0.08, 0.09, 0.10, 0.11, 0.12, 0.13, 0.14, 0.15, 0.16, 0.17, 0.18, 0.19, 0.20 or any range therein In particular embodiments, the nanoparticle is substantially spherical. It would be understood that the term "spherical" means a round body whose surface is at all points equidistant from the centre.

The term "binding agent", as generally used herein refers to a molecule that is capable of binding to an analyte using specific intermolecular interactions. By way of example, the binding agent may have a domain on its surface, or a cavity, which specifically binds to and is therefore complementary to a particular spatial and polar organization of the analyte. Non-limiting examples of binding agents may include antibodies, receptors and ligands.

In an embodiment, the binding agent is an antibody or antibody fragment which binds the analyte in question. Preferably, the antibody is a monoclonal antibody or fragment thereof.

As used herein an "antibody" is or comprises an immunoglobulin. The term "immunoglobulin" includes any antigen-binding protein product of a mammalian immunoglobulin gene complex, including immunoglobulin isotypes IgA, IgD, IgM, IgG and IgE and antigen-binding fragments thereof. Included in the term "immunoglobulin" are immunoglobulins that are chimeric or humanized or otherwise comprise altered or variant amino acid residues, sequences and/or glycosylation, whether naturally occurring or produced by human intervention (e.g. by recombinant DNA technology).

Antibody fragments include Fab and Fab'2 fragments, demibodies, diabodies and single chain antibody fragments (e.g. scVs), although without limitation thereto. Typically, an antibody comprises respective light chain and heavy chain variable regions that each comprise CDR 1, 2 and 3 amino acid sequences. A preferred antibody fragment comprises at least one light chain variable region CDR and/or at least one heavy chain variable region CDR.

Antibodies and antibody fragments may be polyclonal or preferably monoclonal. Monoclonal antibodies may be produced using the standard method as for example, described in an article by Köhler & Milstein, 1975, Nature 256, 495, or by more recent modifications thereof as for example described in Chapter 2 of Coligan et al., CURRENT PROTOCOLS IN IMMUNOLOGY, by immortalizing spleen or other antibody producing cells derived from a production species. It will also be appreciated that antibodies may be produced as recombinant synthetic antibodies or antibody fragments by expressing a nucleic acid encoding the antibody or antibody fragment in an appropriate host cell. Recombinant synthetic antibody or antibody fragment heavy and light chains may be co-expressed from different expression vectors in the same host cell or expressed as a single chain antibody in a host cell. Non-limiting examples of recombinant antibody expression and selection techniques are provided in Chapter 17 of Coligan et al., CURRENT PROTOCOLS IN IMMUNOLOGY and Zuberbuhler et al., 2009, Protein Engineering, Design & Selection 22 169.

It would be appreciated by the skilled person that due to their relatively large size and hydrophilic nature, monoclonal antibodies will not typically fit and/or be immobilized within the pores of the nanoparticles described herein and therefore generally are attached to the exterior surface thereof.

The term "detection agent" as used herein refers to any molecule, compound or material that is detectable or produces a detectable signal or species by one of many detection techniques or technologies as are known in the art such as optical (e.g., fluorescence, chemiluminescence, bioluminescence, colorimetric), electrical, magnetic, spectroscopic, photochemical, radiochemical, radiological, biochemical, immunochemical, or chemical means. As such, the detection agent suitably is or comprises a label.

A wide variety of molecules, compounds or materials may be used as detection agents. Nonlimiting examples of detection agents include a fluorescent agent, enzymes, prosthetic groups, a luminescent agent, a chemiluminescent agent, a bioluminescent agent, fluorescent emitting metal atoms, (e.g., europium (Eu)), radioactive isotopes, electron-dense reagents, and haptens (e.g., digoxigenin).

Nonlimiting exemplary fluorescent detection agents or fluorophores include fluorescein, fluorescein isothiocyanate, rhodamine, 5-dimethylamine-1-napthalenesulfonyl chloride, phycoerythrin, green-, blue- or red-fluorescent protein, quantum dots, umbelliferone, dichlorotriazinylamine fluorescein and the like. Luminescent detection agents may include any of those catalysts or enzymes (e.g., HRP) capable of appropriately oxidizing, for example, luminol, and bioluminescent detection agents may include, for example, luciferase, luciferin, and aequorin.

In particular embodiments, the detection agent is or comprises a fluorescent agent and/or a luminescent agent. In some specific embodiments, the luminescent agent is a chemiluminescent agent or a bioluminescent agent.

In one particularly preferred embodiment, the detection agent is or comprises a quantum dot. A quantum dot is generally understood to comprise a semiconductor crystal particle having a particle diameter of 100 nm or less which has a specific emission property derived from a quantum confinement effect. Quantum dots ordinarily have a particle diameter of from about 1 nm to about 10 nm, and an emission wave length thereof that may be controlled by varying the particle diameter.

Preferably, the plurality of quantum dots have an average particle size in a range from about 1 to about 100 nm. In certain embodiments, the quantum dots have an average particle size in a range from about 1 to about 20 nm (e.g., such as about 5, 6, 7, 8, 9, 10, 11, 12, 13, 14, 15, 16, 17, 18, 19, 20 nm or any range therein). In certain embodiments, quantum dots have an average particle size in a range from about 1 nm to about 20 nm or about 1 nm to about 10 nm. Quantum dots can have an average diameter less than about 150 Angstroms (Å). In certain embodiments, quantum dots having an average diameter in a range from about 12 to about 150 Å can be particularly desirable. However, depending upon the composition, structure, and desired emission wavelength of the quantum dot, the average diameter may be outside of these ranges.

Quantum dots can have various shapes, including, but not limited to, sphere, rod, disk, other shapes, and mixtures of various shaped particles. The particular composition(s), structure, and/or size of a quantum dot can be selected to achieve the desired wavelength of light to be emitted from the quantum dot upon stimulation with a particular excitation source. In essence, quantum dots may be tuned to emit light across the visible spectrum by changing their size. The narrow FWHM of quantum dots can result in saturated colour emission.

A quantum dot can comprise one or more semiconductor materials. Examples of semiconductor materials that can be included in a quantum dot (including, e.g., semiconductor nanocrystal) include, but are not limited to, a Group IV element, a Group II-VI compound, a Group II-V compound, a Group III-VI compound, a Group III-V compound, a Group IV-VI compound, a Group I-III-VI compound, a Group II-IV-VI compound, a Group II-IV-V compound, an alloy including any of the foregoing, and/or a mixture including any of the foregoing, including ternary and quaternary mixtures or alloys. A non-limiting list of examples include ZnO, ZnS, ZnSe, ZnTe, CdO, CdS, CdSe, CdTe, MgS, MgSe, GaAs, GaN, GaP, GaSe, GaSb, HgO, HgS, HgSe, HgTe, InAs, InN, InP, InSb, AlAs, AlN, AlP, AlSb, TlN, TlP, TlAs, TlSb, PbO, PbS, PbSe, PbTe, Ge, Si, an alloy including any of the foregoing, and/or a mixture including any of the foregoing, including ternary and quaternary mixtures or alloys.

In certain embodiments, quantum dots can comprise a core comprising one or more semiconductor materials and a shell comprising one or more semiconductor materials, wherein the shell is disposed over at least a portion, and preferably all, of the outer surface of the core. A quantum dot including a core and shell is also referred to as a "core/shell" structure.

A shell can be a semiconductor material having a composition that is the same as or different from the composition of the core. The shell can comprise an overcoat including one or more semiconductor materials on a surface of the core. Examples of semiconductor materials that can be included in a shell include, but are not limited to, a Group IV element, a Group II-VI compound, a Group II-V compound, a Group III-VI compound, a Group III-V compound, a Group IV-VI compound, a Group I-III-VI compound, a Group II-IV-VI compound, a Group II-IV-V compound, alloys including any of the foregoing, and/or mixtures including any of the foregoing, including ternary and quaternary mixtures or alloys. Examples include, but are not limited to, ZnO, ZnS, ZnSe, ZnTe, CdO, CdS, CdSe, CdTe, MgS, MgSe, GaAs, GaN, GaP, GaSe, GaSb, HgO, HgS, HgSe, HgTe, InAs, InN, InP, InSb, AlAs, AlN, AlP, AlSb, TlN, TlP, TlAs, TlSb, PbO, PbS, PbSe, PbTe, Ge, Si, an alloy including any of the foregoing, and/or a mixture including any of the foregoing. For example, ZnS, ZnSe or CdS overcoatings can be grown on CdSe or CdTe semiconductor nanocrystals.

In a core/shell quantum dot, the shell or overcoating may comprise one or more layers. The overcoating can comprise at least one semiconductor material which is the same as or different from the composition of the core. Preferably, the overcoating has a thickness from about one to about ten monolayers. An overcoating can also have a thickness greater than ten monolayers. In certain embodiments, more than one overcoating can be included on a core. In certain embodiments, the surrounding "shell" material can have a band gap greater than the band gap of the core material. In certain other embodiments, the surrounding shell material can have a band gap less than the band gap of the core material.

In certain embodiments, the shell can be chosen so as to have an atomic spacing close to that of the "core" substrate. In certain other embodiments, the shell and core materials can have the same crystal structure.

Methods of making quantum dots are known in the art. One example of a method of manufacturing a quantum dot is a colloidal growth process. Colloidal growth occurs by injection an M donor and an X donor into a hot coordinating solvent. One example of a preferred method for preparing monodisperse quantum dots comprises pyrolysis of organometallic reagents, such as dimethyl cadmium, injected into a hot, coordinating solvent. This permits discrete nucleation and results in the controlled growth of macroscopic quantities of quantum dots. The injection produces a nucleus that can be grown in a controlled manner to form a quantum dot. The reaction mixture can be gently heated to grow and anneal the quantum dot. Both the average size and the size distribution of the quantum dots in a sample are dependent on the growth temperature. The growth temperature for maintaining steady growth increases with increasing average crystal size. Resulting quantum dots are members of a population of quantum dots. As a result of the discrete nucleation and controlled growth, the population of quantum dots that can be obtained has a narrow, monodisperse distribution of diameters. The monodisperse distribution of diameters can also be referred to as a "size".

Enhancement or quenching of emission by the QDs may be achieved by adjusting the size of the QD, changing structure or adding other materials. Quenching may help increase light efficiency. Higher efficiency means, for example, that more red light or green light will be produced from red QDs and green QDs when using the same light source. When QDs are stuck to each other, for example, a red QD is stuck to a green QD, the red QD may be re-excited by the green QD, which may increase the light efficiency of the red light, but may reduce the light efficiency of the green light. Thus, it is desirable to have the QDs separated from each other in the matrix. Given the arrangement of pores and pore sizes of the nanoparticles described herein, there will be less likely for the QDs immobilized thereon to stick to each other and thus this arrangement may improve light efficiency. Therefore, quenching may be minimized to reduce manufacturing cost.

The QDs to be immobilized on the nanoparticles described herein are preferably selected based on the desired peak emission wavelength or combinations of wavelengths desired for the particular end-use application intended for said nanoparticle. When quantum dots that emit light with peak emission wavelengths that differ from that of other quantum dots included in particular embodiments, the amounts of each are selected based on the desired light output. Such determination can be readily made by the person of ordinary skill in the relevant art.

A detection agent can also be or comprise a detectable enzyme or an enzyme that catalyses the formation of a detectable species, such as alkaline phosphatase, horseradish peroxidase, β-galactosidase, acetylcholinesterase, glucose oxidase and the like. Such an enzyme is typically capable of generating a detectable signal by converting a substrate thereof. It would be understood that for the present invention an enzyme may also be considered, for example, a luminescent agent (i.e., a chemiluminescent agent and/or bioluminiscent agent), depending on the particular substrate which is to applied thereto and the subsequent reporter signal produced therefrom.

The nanoparticle of the present invention can also be derivatized with a prosthetic group (e.g., streptavidin/biotin and avidin/biotin). For example, a nanoparticle can be derivatized with biotin and detected through indirect measurement of avidin or streptavidin binding.

A detection agent can also be or comprise a radioactive isotope, such as, but not limited to, α-, β-, or γ-emitters; or β- and γ-emitters. Such radioactive isotopes may include, but are not limited to, iodine ($^{131}$I or $^{125}$I), yttrium ($^{90}$Y), lutetium ($^{177}$Lu), actinium ($^{225}$Ac), praseodymium ($^{142}$Pr or $^{143}$Pr), astatine ($^{211}$At), rhenium ($^{186}$Re or $^{187}$Re), bismuth ($^{212}$Bi or $^{213}$Bi), indium ($^{111}$In), technetium ($^{99m}$Tc), phosphorus ($^{32}$P), rhodium ($^{188}$Rh), sulfur ($^{35}$S), carbon ($^{14}$C), tritium ($^{3}$H), chromium ($^{51}$Cr), chlorine ($^{36}$Cl), cobalt ($^{57}$Co or $^{58}$Co), iron ($^{59}$Fe), selenium ($^{75}$Se), and gallium ($^{67}$Ga).

Suitably, the method of the present aspect further includes the step of detecting the nanoparticle bound to said analyte. Detecting an analyte, and by extension, determining, assessing, evaluating, assaying or measuring an analyte's levels, may be performed by any technique known in the art that is capable of detecting the particular detection agent of the nanoparticle bound thereto.

By way of example, detection may include flow cytometry, ELISA, immunoblotting, immunoprecipitation, in situ hybridization, immunohistochemistry, immuncytochemistry, confocal microscopy, confocal scanner, colorimetric detection, although without limitation thereto. Suitable techniques may be adapted for high throughput and/or rapid analysis such as using protein arrays such as a TissueMicroArray™ (TMA), MSD MultiArrays™ and multiwell ELISA, although without limitation thereto. It would be understood that the detection method to be utilized may be at least partly dependent upon the binding agent and/or the detection agent of the nanoparticle.

Suitably, the method of the present aspect further includes the step of producing a reporter signal from the detection agent. In certain embodiments, the step of producing a reporter signal comprises contacting the nanoparticle bound to the analyte with a substrate of the detection agent so as to facilitate the production of a reporter signal therefrom. By way of example, when the nanoparticle is functionalized with a detectable enzyme, it can be detected by adding a substrate that the enzyme uses to produce a detectable reaction product (i.e., a reporter signal).

For example, when the detection agent is horseradish peroxidase, the addition of hydrogen peroxide and diaminobenzidine as substrates leads to a detectable coloured reaction product or reporter signal. Additional substrates for HRP may include 2,2'-Azinobis [3-ethylbenzothiazoline-6-sulfonic acid]-diammonium salt (ABTS), o-phenylenediamine dihydrochloride (OPD), luminol and 3,3',5,5'-tetramethylbenzidine (TMB), although without limitation thereto. Nonlimiting examples of substrates for alkaline phosphatase include p-Nitrophenyl Phosphate (PNPP), 5-bromo, 4-chloro, 3-indolylphosphate (BCIP) and Nitro-Blue Tetrazolium (NBT). Nonlimiting examples of substrates for β-galactosidase include o-nitrophenyl-β-D-galactopyranoside (ONPG) and 5-bromo-4-chloro-3-indolyl-β-D-galactopyranoside (BCIG or X-gal).

In certain other embodiments, the step of producing the reporter signal comprises contacting the detection agent with electromagnetic radiation so as to facilitate the production of said reporter signal therefrom. In this regard, the step of producing a reporter signal may comprise exciting the detection agent with, for example, visible or infrared light of a suitable wavelength, so that the detection agent fluoresces to produce light of a certain wavelength that may then be detected. By way of example, quantum dots may be excited by certain wavelengths of light to then fluoresce, in doing so, emitting light that may be detected.

As would be understood by the skilled person, the nanoparticle described herein may be first subjected to a surface treatment, which are well known in the art and, for example, described herein, as necessary, so as to apply an anchoring group thereto and facilitate immobilization of the detection agent thereon. By way of example, such surface treatment may result in the addition of an anchoring group selected from the group consisting of an amino group, a thiol group, a carboxyl group, a polyethylene glycol group, a peptide group and any combination thereof.

It would be appreciated that the method may further include the step of detecting the reporter signal produced by the nanoparticle. This may be performed by any means known in the art, such as those hereinbefore described.

In particular embodiments, the sample is or comprises a biological sample, such as that taken from a patient or subject. To this end, a biological sample may comprise tissue (e.g., a biopsy), blood, serum, plasma, cerebrospinal fluid, urine, or other bodily fluid, or a filtrate of a bodily fluid, from a subject. In one embodiment, the biological sample is, comprises, or is obtained from a non-cellular source. To this end, the biological sample may be serum, plasma, or cerebrospinal fluid, although without limitation thereto.

In some embodiments, the method for detecting an analyte may be used, for example, to determine whether or not a subject has a particular disease, disorder or condition of interest may be performed in "high throughput" diagnostic tests or procedures such as performed by commercial pathology laboratories, at the point-of-care or in hospitals. Furthermore or alternatively, the method of the present aspect may be used to confirm a diagnosis of a particular disease, disorder or condition, such as that initially detected by a different or alternative diagnostic test or procedure.

In other embodiments, the sample is or comprises an environmental sample. This particular embodiment of the invention may involve the acquisition of indoor samples, such as from homes, schools, commercial buildings and workplaces, and/or outdoor samples. For example, to detect and/or monitor, for example, toxin or allergen levels in a household environment, a suitable sample may be collected dust. Other suitable samples may include, but are not limited to, soil, water, air, a foodstuff or a drink.

In another aspect, the invention provides a diagnostic and/or screening kit comprising:

(a) a nanoparticle for detecting an analyte, wherein the nanoparticle comprises:
(i) a core;
(ii) a pore extending radially from said core;
(iii) a binding agent for binding the analyte; and
(iv) a detection agent immobilized within said pore; and
(b) instructions for use.

It would be appreciated that certain embodiments of this aspect may be used for detecting and/or monitoring the levels of one or more analytes in a subject. Further embodiments of this aspect may be used in detecting and/or monitoring the presence of one or more analytes in the environment.

The nanoparticle of this aspect may be one as hereinbefore described. Preferably, the nanoparticle is a silica nanoparticle.

The kit may further comprise additional diagnostic reagents such as substrates for the detection agent (e.g., Luminol, ABTS or NBT), as are known in the art and hereinbefore described. The binding agent and/or detection agent may also be as hereinbefore described.

Suitably, the kit of the present aspect is for use in the method of the previous aspect.

In a further aspect, the invention provides a method for generating a nanoparticle displaying an anchoring group including the steps of:
(i) providing a metal or metalloid source;
(ii) contacting the metal or metalloid source with a base and optionally a surfactant in a liquid environment;
(iii) contacting the product of step (ii) with a compound displaying the anchoring group;
to thereby generate the nanoparticle displaying an anchoring group.

Preferably, the nanoparticle is selected from those hereinbefore described and so the metal or metalloid source is selected accordingly.

In one embodiment, the metal or metalloid source is silica and the compound displaying the anchoring group is a silicate displaying the anchoring group.

In one embodiment, the method further comprises the step of treating the nanoparticle displaying an anchoring group to remove remaining surfactant template.

In one embodiment, the metal or metalloid source is contacted with the surfactant in the liquid environment. In an alternative embodiment, the metal or metalloid source is not contacted with the surfactant in the liquid environment.

The removal of the surfactant may be by acid treatment.

In one embodiment, the metal or metalloid source is further contacted with an alcohol in the liquid environment.

Suitably, the anchoring group is selected from the group consisting of a thiol, an amine, a carboxyl group, a polyethylene glycol group, a carbon chain and any combination thereof. Preferably, the anchoring group is a thiol. In this regard, the silicate displaying the anchoring group is suitably a thiol-containing alkoxysilane, such as MPTMS (3-mercaptopropyl)-trimethoxysilane and MPDMS (3-mercaptopropyl)-methyl-dimethoxysilane.

In one embodiment, the surfactant may be a quaternary ammonium surfactant as are well known in the art. In one preferred embodiment, the surfactant is or comprises an alkyl trimethylammonium bromide, such as cetyl trimethylammonium bromide (CTAB).

In embodiments wherein the source is a silica source, it may be any hydrolyzable silica source known in the art. In a preferred embodiment, the hydrolyzable silica source is or comprises an alkyl orthosilicate, such as TEOS and TMOS.

Suitably, the silica nanoparticle of this aspect is that hereinbefore described.

In one embodiment, a delay period of at least 5 minutes (e.g., 5 min, 10 min, 15 min, 20 min, 25 min, 30 min, 35 min, 40 min, 45 min, 50 min, 55 min, 60 min, 65 min, 70 min, 75 min, 80 min, 85 min, 90 min and any range therein) is provided between steps (ii) and (iii) so as to allow for the silica nanoparticle to form to a certain extent before the anchoring group is introduced. Surprisingly, it has been found that introducing a delay of 5 minutes or longer between the step at which the base, surfactant and metal or metalloid source and combined and the step wherein the compound displaying the anchoring group is introduced allows higher thiol contents in the resulting nanoparticles to be achieved. Without wishing to be bound by theory, it is believed that the delayed introduction of the anchoring group compound allows the nanoparticle formation to first proceed to an extent without any anchoring groups incorporated so that later introduction of the anchoring group compound concentrates the resulting anchoring groups at or close to the surface of the pores of the particles, as opposed to greater internalization of the anchoring groups where a greater proportion of the groups may not be available at the surface. In cases where the anchoring group is a thiol group, sulfur contents as measured by CHNS elemental analysis in the range 1 to 10% by weight of the nanoparticle may be achieved.

In one aspect, the invention provides a composition comprising a nanoparticle dispersed in and/or on a substrate, wherein the nanoparticle comprises:
  (i) a core;
  (ii) a pore extending radially from said core; and
  (iii) a plurality of quantum dots immobilized within said pore.

It will be appreciated that the quantum dot of the present aspect may be that as hereinbefore described.

Suitably, the nanoparticle of this aspect is one as hereinbefore described. Preferably, the nanoparticle is a silica nanoparticle.

With respect to the aforementioned pore size and shape of the nanoparticles described herein, it is presumed that such a design provides not only a significantly large surface area available for QD loading thereon, but also easy loading of QDs into the porous structure. Accordingly it is proposed that significant signal amplification in electronic displays may be a function, at least in part, of such a pore design.

It will be apparent to the skilled artisan that pore size, to some degree, may be determined by the required number and/or particular QDs to be immobilized therein. By way of example, a greater number of QDs and/or larger QDs will typically require a larger pore size. Accordingly, the average pore size of the nanoparticle may vary with the particular QD to be immobilized therein.

With respect to particle size, it would be appreciated by the skilled artisan that when designing a nanoparticle for a particular application, there exists a need to find a delicate balance between the appropriate size of loading surfaces to maximize the amount of QDs loaded thereon (i.e., an increase of the particle size and/or pore size) and a small enough particle volume so as to be incorporated within an optical or display layer or container of acceptable dimensions (i.e., a decrease of the particle size). Accordingly, the average particle size of the nanoparticle may vary with the particular application (e.g., LCDs, solar cells, LEDs etc) for which it is to be used.

In some embodiments the nanoparticles of the present invention suitably demonstrate a high degree of monodispersity (i.e., a substantially uniform particle size) in order that a consistent strength of signal (i.e., emitted light) is generated by the QDs immobilized thereon. In order to ensure reliable and consistent emission by the QD-containing nanoparticles, it is advantageous to have a tight distribution of particle sizes, and consequently a high degree of uniformity in the number of QDs present on each nanoparticle to produce a uniform signal intensity. To this end, the polydispersity index (PDI) of the nanoparticles of the present aspect may be that as hereinbefore described.

The total amount of quantum dot-containing nanoparticles included in the composition of the invention is preferably in a range from about 0.01 to about 25 weight percent (e.g., about 0.01, 0.05, 0.1, 0.25, 0.5, 0.75, 1.0, 2.0, 3.0, 4.0, 5.0, 6.0, 7.0, 8.0, 9.0, 10.0, 11.0, 12.0, 13.0, 14.0, 15.0, 16.0, 17.0, 18.0, 19.0, 20.0, 21.0, 22.0, 23.0, 24.0, 25 weight percent), and any weight percent in between. For example, an amount in a range from about 0.05 weight percent to about 15 weight percent, or about 0.05 weight percent to about 5 weight percent can be desirable for various applications. Such amounts are not intended to be limiting. An amount outside of such ranges may also be determined to be useful. The amount of quantum dot-containing nanoparticles included in the composition can vary based on the particular end application.

In particular embodiments, the composition can further include one or more additional components or agents, including, for example, but not limited to, one or more of a scatterer, a thixotrope, and an emission stabilizer, as are known in the art.

As used throughout, "dispersed" includes uniform (i.e., substantially homogeneous) as well as nonuniform (i.e., substantially heterogeneous) distribution or placement of the QD-containing nanoparticles in and/or on the substrate. Additionally, the QD-containing nanoparticles as described herein can be dispersed in and/or on the substrate, such as a matrix material, using any suitable method, for example, mixing the QD-containing nanoparticles in a polymer and casting a film; mixing the QD-containing nanoparticles with monomers and polymerizing them together; mixing the QD-containing nanoparticles in a sol-gel, or any other method known to those skilled in the art. In particular embodiments, the QD-containing nanoparticles are enclosed or encased within the substrate. It should be noted that the QD-containing nanoparticles are suitably uniformly distributed throughout the composition, though in further embodiments they can be distributed according to an application-specific uniformity distribution function. Additionally, the QD-containing nanoparticles may be arranged in layers either in a monolayer or multiple layers (e.g., 2, 3, 4, 5, 6, 7, 8, 9, 10 . . . 99, 100 etc) thick.

The composition described herein can be any desirable size, shape, configuration and thickness. For example, the composition can be in the form of layers, as well as other shapes, for example, discs, spheres, cubes, blocks, tubular configurations and the like. While the various compositions can be any thickness required or desired, suitably, the compositions are in the order of about 100 mm in thickness (i.e., in one dimension), and down to less than about 1 mm in thickness and even down to on the order of the diameter of the particular nanoparticles contained in the composition in thickness. In other embodiments, the composition can be in the form of a film in the order of, for example, 10's to 100's of microns in thickness.

The QDs to be immobilized on the nanoparticles described herein are preferably selected based on the desired peak emission wavelength or combinations of wavelengths desired for the particular end-use application intended for said nanoparticle. The QDs may be those as described above.

When quantum dots that emit light with peak emission wavelengths that differ from that of other quantum dots included in particular embodiments, the amounts of each are selected based on the desired light output. Such determination can be readily made by the person of ordinary skill in the relevant art. For example, the ratio of quantum dots with different peak emissions that are used in the composition is determined by the emission peaks of the quantum dots used. For example, when quantum dots capable of emitting green light having a peak centre wavelength in a range from about 514 nm to about 540 nm, and any wavelength in between whether overlapping or not, and quantum dots capable of emitting red light having a peak centre wavelength in a range from about 615 nm to about 640 nm, and any wavelength in between whether overlapping or not, are used in the composition, the ratio of the weight percent green-emitting quantum dots to the weight percent of red-emitting quantum dots can be in a range from about 12:1 to about 1:1 (e.g., about 12:1, 11:1, 10:1, 9:1, 8:1, 7:1, 6:1, 5:1, 4:1, 3:1, 2:1, 1:1), and any ratio in between whether overlapping or not.

In certain embodiments of the present invention, the plurality of quantum dots emit light at a wavelength characteristic of red light. In certain preferred embodiments, quantum dots capable of emitting red light emit light having a peak centre wavelength in a range from about 615 nm to about 635 nm, and any wavelength in between whether overlapping or not. For example, the quantum dots can be capable or emitting red light having a peak centre wavelength of, for example, about 630 nm, about 625 nm, about 620 nm, and/or about 615 nm.

In certain embodiments of the present invention, the plurality of quantum dots emit light at wavelengths characteristic of green light. In certain preferred embodiments, quantum dots capable of emitting green light emit light having a peak centre wavelength in a range from about 520 nm to about 545 nm, and any wavelength in between whether overlapping or not. For example, the quantum dots can be capable or emitting green light having a peak centre wavelength of, for example, about 520 nm, about 525 nm, about 535 nm, and/or about 540 nm.

As used throughout, a plurality of QDs means more than one QD (i.e., 2, 3, 4, 5, 10, 100, 1,000, 1,000,000, etc., QDs). The compositions will suitably comprise nanoparticles including QDs having the same composition, though, in further embodiments, the plurality of QDs can be various different compositions. For example, the QDs may all emit at the same wavelength, or in further embodiments, the compositions can comprise nanoparticles having QDs that emit at different wavelengths.

Accordingly, in one embodiment, the nanoparticles include a plurality of quantum dots that include at least one population of QDs capable of emitting red light and at least one population of QDs capable of emitting green light upon excitation by a blue light source. The luminescent nanocrystal wavelengths and concentrations can be adjusted to meet the optical performance required.

As used herein, visible light is electromagnetic radiation with wavelengths between about 380 and about 780 nanometers that is visible to the human eye. Visible light can be separated into the various colours of the spectrum, such as red, orange, yellow, green, blue, indigo and violet. As used herein, blue light comprises light between about 435 nm and about 500 nm, green light comprises light between about 520 am and 565 nm and red light comprises light between about 625 nm and about 740 nm in wavelength.

The substrate may be any suitable material as are known in the art. Preferably, the substrate allows light from a light source to pass through (i.e., substantially translucent or substantially transparent). For example, in certain embodiments, the substrate is preferably at least 70%, more preferably at least 80%, and most preferably at least 90%, transparent to light to be colour converted by the quantum dots. In certain embodiments, the substrate is preferably at least 70%, more preferably at least 80%, and most preferably at least 90%, transparent and light emitted by the quantum dots. In particular embodiments, the substrate comprises a material that is transparent to light within a predetermined range of wavelengths.

Nonlimiting examples of substrates useful in various embodiments and aspects of the invention described herein include polymers, monomers, resins, binders, glasses, metal oxides, and other nonpolymeric materials.

Preferred substrates include polymeric and non-polymeric materials that are at least partially transparent, and preferably fully transparent, to preselected wavelengths, including ranges thereof, of visible and non-visible light. In certain embodiments, the preselected wavelengths can include wavelengths of light in the visible (e.g., 400-700 nm), ultraviolet (e.g., 10-400 nm), and/or infrared (e.g., 700 nm-12 μm) regions of the electromagnetic spectrum. Examples of preferred substrates include, but are not limited to, glass or a transparent resin. In particular, a resin such as a non-curable resin, heat-curable resin, or photocurable resin is suitably used from the viewpoint of processability. As specific examples of such a resin, in the form of either an oligomer or a polymer, a melamine resin, a phenol resin, an alkyl resin, an epoxy resin, a polyurethane resin, a maleic resin, a polyamide resin, polymethyl methacrylate, polyacrylate, polycarbonate, polyvinyl alcohol, polyvinylpyrrolidone, hydroxyethylcellulose, carboxymethylcellulose, copolymers containing monomers forming these resins, and the like.

In particular embodiments, the substrate is or comprises a matrix material, such as a polymeric matrix. To this end, suitable polymers include any polymer known to the ordinarily skilled artisan that can be used for such a purpose, including polymeric materials, organic and inorganic oxides. By way of example, the matrix material may be a polymer, such as polyacrylate, polystyrene, polyimide, polyacrylamide, polyethylene, polyvinyl, poly-diacetylene, polyphenylene-vinylene, polypeptide, polysaccharide, polysulfone, polypyrrole, polyimidazole, polythiophene, polyether, epoxies, silica glass, silica gel, siloxane, polyphosphate, hydrogel, agarose, cellulose, and the like.

In certain embodiments, the substrate is flexible. Alternatively, the substrate may be rigid.

Compositions described herein can be layers, encapsulants, coatings, sheets or films. It should be understood that in embodiments described herein where reference is made to a layer, polymeric layer, matrix, sheet or film, these terms are used interchangeably, and the embodiment so described is not limited to any one type of composition, but encompasses any substrate or layer described herein or known in the art.

As would be understood by the skilled person, the nanoparticle described herein may be first subjected to a surface treatment, which are well known in the art, as necessary, so as to apply an anchoring group thereto and facilitate immobilization of the QDs thereon. By way of example, such surface treatment may result in the addition of an anchoring group selected from the group consisting of an amino group, a thiol group, a carboxyl group, a polyethylene glycol group, a peptide group and any combination thereof.

In certain embodiments, the quantum dot-containing layer can be sealed between two or more substrates (such as a first substrate and a second substrate). Examples of preferred substrates in this regard include glass, polycarbonate, acrylic, quartz, sapphire, a polymeric material such as plastic or silicone (e.g. but not limited to thin acrylic, epoxy, polycarbonate, PEN, PET, PE).

In other embodiments, the composition can be included in a hollow container or cavity portion of a tubular-like structural member (e.g., a tube, hollow capillary, hollow fiber, etc.) that can be open at either or both ends. Preferably open end(s) of the member are hermetically sealed after the composition is included therein. Examples of sealing techniques include but are not limited to, (1) contacting an open end of a tube with an epoxy, (2) drawing the epoxy into the open end due to shrinkage action of a curing resin, or (3) covering the open end with a glass adhering metal such as a glass adhering solder or other glass adhering material, (4) hot glue; and (5) melting the open end by heating the glass above the melting point of the glass and pinching the walls together to close the opening to form a molten glass hermetic seal.

In another aspect, the invention provides a display device comprising:
(i) a light source
(ii) a light emitting layer comprising the composition hereinbefore described and optically coupled to the light source; and
(iii) a display.

In one embodiment, the light source is or comprises a blue light source, such as a blue LED.

In one embodiment, the composition is or comprises a film. In another embodiment, the composition is sealed within a substantially transparent container. Preferably, the substantially transparent container is substantially transparent to preselected wavelengths, including ranges thereof, of visible and non-visible light, such as those provided above.

In one embodiment, the display is or comprises a liquid crystal module.

As used herein, "optically coupled" means that components (e.g. the light source and the light emitting layer) are positioned so that light is able to pass from one component to another component without substantial interference.

In certain embodiments, the display device described herein suitably comprises one or more additional elements traditionally found in, for example, LED-based display devices. Such elements include, but are not limited to, one or more of a light guide plates, a diffuser, a horizontal brightness enhancement film (BEF), a vertical BEF, and a reflector. Suitably, orientations of these elements, their manufacture and incorporation in display systems are well known in the art.

In embodiments, various display devices are provided herein that are suitably used in any number of applications. As used herein, a "display device" refers an arrangement of elements that allow for the visible representation of data or the like on a display. Suitable displays include various flat, curved or otherwise-shaped screens, films, sheets or other structures for displaying information visually to a user. Display devices described herein can be included in, for example, devices encompassing a liquid crystal display (LCD), televisions, computers, mobile phones, smart phones, personal digital assistants (PDAs), gaming devices, electronic reading devices, digital cameras, and the like.

Figure 10:
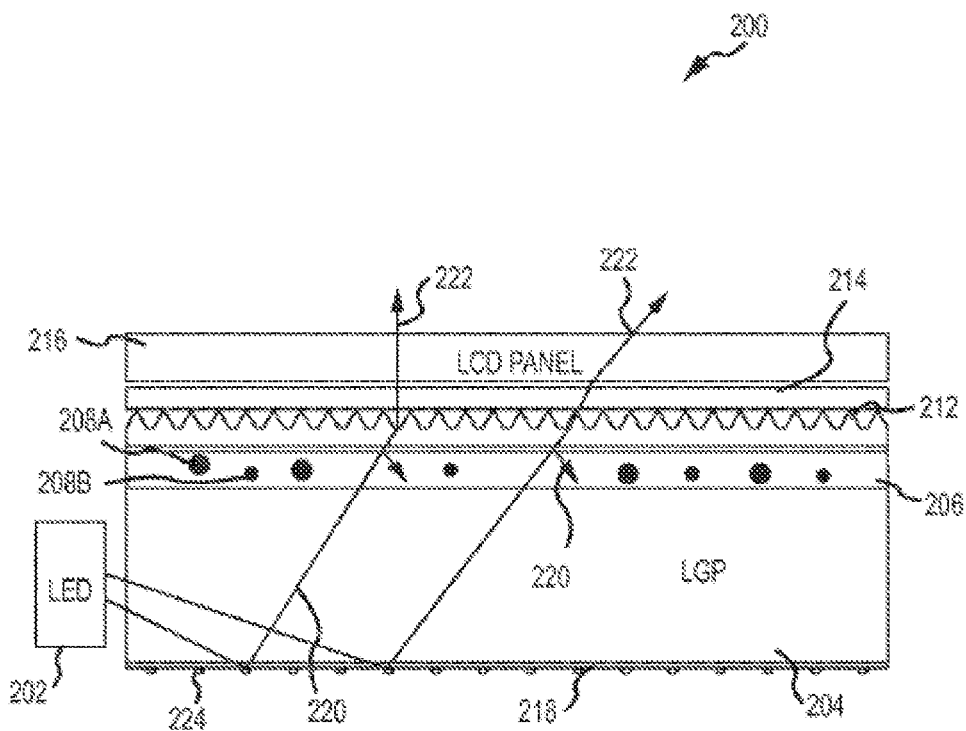
FIG. 10. An embodiment of a display device of the invention.

An exemplary embodiment of a display device 200 of the invention is shown in FIG. 10. The display device 200 includes a light source 202, a light guide panel (LGP) 204, a light emitting layer 206 comprising the composition described herein, and an LCD panel 216. The QD enhanced display 200 may also optionally include a prism 212 and a double brightness enhanced film (DBEF) 214. The light source 202 may be a blue light-emitting diode (LED) or a blue Gallium Nitride (GaN) LED.

To produce even lighting, a blue light from the light source 202 first passes through the LGP 204 that may include a series of unevenly-spaced bumps or light extraction features 224 and a reflector 218 behind the light extraction features 224. The LGP 204 diffuses the blue light through the series of unevenly-spaced bumps or light extraction features 224, as shown by blue light 220. The density of the bumps or light extraction features increases further away from the light source 202. The front face of the LGP 204 faces the LCD panel 216 and the back of the LGP 204 has the reflector 218, which guides otherwise wasted light back toward the LCD panel 216. In one example, the reflector 218 may be made of highly reflective material, such as white polyethylene terephthalate (PET) and in one embodiment reflects about 97% of all light impacting its surface.

The LCD panel 216 also includes colour filters arranged in subpixels, a front polarizer, a rear polarizer, and liquid crystal as well as electrodes, similar to conventional LCD panels as are known in the art. Generally, there is an air space between the LCD panel 216 and the DBEF 214.

Generally, the light emitting layer 206 is configured to transmit a portion of the blue light 220 from the light source 202 such that white light 222 comes out of the light emitting layer 206. The light emitting layer 206 includes a group of red quantum dots (QDs) 208A and green QDs 208B, which actively convert the blue light 220 from the LED into red light and green light through the quantum dots. When the QDs 208A and 208B are irradiated by the blue light from the light source 202, the blue light causes the QDs 208A and 208B to photoluminescence and thereby produce secondary light. The colour of the secondary light is generally a function of the size, size distribution and composition of the QDs 208A and 208B.

As shown in FIG. 10, the light emitting layer 206 further includes a substrate in which the QDs 208A and 208B are disposed. The substrate allows light from the light source 202 to pass through.

It will be appreciated by those skilled in the art that the QD enhanced display may vary in configuration. For example, other lit configurations may be used, including a direct lit configuration in some embodiments. The prism 212 may also be removed or substituted by a further brightness enhancement component in an alternative embodiment. The DBEF 214 may be removed in another embodiment.

In yet another aspect, the invention provides a light emitting diode device comprising:
(i) a cathode;
(ii) an electron transport layer on the cathode;
(iii) a light emitting layer formed on the electron transport layer, wherein the light emitting layer comprises the composition hereinbefore described;
(iv) a hole transport layer on the light emitting layer; and
(v) an anode formed on the hole transport layer.

It would be appreciated that a light emitting diode (LED) device is a semiconductor light emitting component. Different from the traditional incandescent bulb which illuminates by a high current applied to heat the filament, the LED only requires a low current to emit the equivalent light. LED is based on the fact that in semiconductor materials when electrons are binding with holes the energy released is revealed in the form of emitting light. Due to having the advantages of, for example, small volume, long lifespan, low driving voltage, low power consumption, quick response, excellent shock resistance and good monochromaticity, the LED is widely used in light emitting component, such as in various electrical appliances.

In particular embodiments, the light emitting layer which comprises the QD-containing nanoparticles of the present invention emits light of a single wavelength (e.g., blue). In alternative embodiments, the light emitting layer emits lights (i.e., a first light, a second light etc.) of two or more wavelengths. In one preferred embodiment, the light emitting layer emits lights (i.e., a first light, a second light and a third light) of three different wavelengths (e.g., red, blue and green) in the same area; therefore, compared with the conventional light source which employs individual LEDs to mix lights, this LED typically demonstrates a better colour rendering index.

In still another aspect, the invention provides a solar cell, comprising:
(i) an electron conductor layer; and
(ii) an electron emitting layer comprising the composition hereinbefore described and coupled to the electron conductor layer.

With respect to solar cells, it would be understood by the skilled artisan that solar cells are ideally able to harvest or capture as much of the incident solar light or energy as possible and subsequently convert it into electrons. In this regard, it would be apparent that the QD-containing nanoparticles described herein may be configured to essentially present a dense 3D array of QDs to incoming light that acts like a tight net to capture incident photons with high efficiency and subsequently transmit the electrons produced to the electron conductor layer.

In a preferred embodiment, the electron emitting layer which comprises the QD-containing nanoparticles of the present invention is adapted to absorb light of two or more wavelengths. In one particularly preferred embodiment, the electron emitting layer is adapted to absorb light (e.g., a first light, a second light, a third light etc.) substantially across the electromagnetic spectrum.

Accordingly, the electron emitting layer preferably contains two or more groups (i.e., 2, 3, 4, 5 etc.) of quantum dots, wherein each group of quantum dots is adapted to absorb light within a portion of the electromagnetic spectrum. By way of example, the electron emitting layer may comprise a first group of quantum dots and a second group of quantum dots, wherein the first group of quantum dots is adapted to absorb light within a first portion of the electromagnetic spectrum and the second group of quantum dots is adapted to absorb light within a second portion of the electromagnetic spectrum.

It would be apparent to the skilled artisan, that the electron conductor layer may comprise one or more suitable conducting materials that are typically used in the manufacture of a QD solar cell module or component, as are well known in the art.

In a related aspect, the invention provides a method for emitting light, said method including the steps of:
(i) providing a light emitting layer comprising the composition hereinbefore described; and
(ii) exciting the light emitting layer with electromagnetic radiation of a frequency that is capable of absorption by one or more of the quantum dots therein;
to thereby emit light.

In one embodiment, the method of the present aspect further includes the step of receiving the emitted light by a display.

In particular embodiments, the light emitting layer is a component part of a display device, such as an LCD display. In other embodiments, the light emitting layer is a component part of an LED, such as a blue LED.

In a further aspect, the invention provides a method for emitting electrons, said method including the steps of:
(i) providing an electron emitting layer comprising the composition hereinbefore described; and
(ii) exciting the electron emitting layer with electromagnetic radiation of a frequency that is suitable for absorption by one or more of the quantum dots therein;
to thereby emit electrons.

In one embodiment, the method of the present aspect further includes the step of receiving the emitted electrons by an electron conductor layer of a solar cell. Accordingly, in particular embodiments, the electron emitting layer is a component part of a solar cell.

In a further aspect, the invention provides a method for generating a nanoparticle having a plurality of quantum dots immobilized thereon including the steps of:
(i) providing a metal or metalloid source;
(ii) contacting the metal or metalloid source with a base and optionally a surfactant in a liquid environment;
(iii) contacting the product of step (ii) with a compound displaying an anchoring group;
(iv) contacting the product of step (iii) with said quantum dots;
to thereby generate the nanoparticle having the plurality of quantum dots immobilized thereon.

Preferably, the nanoparticle is selected from those hereinbefore described and so the metal or metalloid source is selected accordingly. Similarly, the plurality of quantum dots is suitably as described above.

In one embodiment, the metal or metalloid source is a source of silica and the compound displaying the anchoring group is a silicate displaying the anchoring group.

In one embodiment, the method further comprises the step of treating the nanoparticle displaying an anchoring group to remove remaining surfactant template.

The removal of the surfactant may be by acid treatment.

In one embodiment, the metal or metalloid source is further contacted with an alcohol in the liquid environment.

Suitably, the anchoring group is selected from the group consisting of a thiol, an amine, a carboxyl group, a polyethylene glycol group, a carbon chain and any combination thereof. Preferably, the anchoring group is a thiol. In this regard, the silicate displaying the anchoring group is suitably a thiol-containing alkoxysilane, such as MPTMS (3-mercaptopropyl)-trimethoxysilane and MPDMS (3-mercaptopropyl)-methyl-dimethoxysilane.

In one embodiment, a delay period of at least 5 minutes (e.g., 5 min, 10 min, 15 min, 20 min, 25 min, 30 min, 35 min, 40 min, 45 min, 50 min, 55 min, 60 min, 65 min, 70 min, 75 min, 80 min, 85 min, 90 min and any range therein) is provided between steps (ii) and (iii) so as to allow for the silica nanoparticle to form to a certain extent before the anchoring group is introduced. As previously described, it has been surprisingly found that introducing a delay of 5 minutes or longer between the step at which the base, surfactant and metal or metalloid source and combined and the step wherein the compound displaying the anchoring group is introduced allows higher thiol contents in the resulting nanoparticles to be achieved. Accordingly, the present method is preferably performed in this manner.

In one embodiment, the metal or metalloid source is contacted with the surfactant in the liquid environment. In an alternative embodiment, the metal or metalloid source is not contacted with the surfactant in the liquid environment.

In one embodiment, the surfactant may be a quaternary ammonium surfactant as are well known in the art. In one preferred embodiment, the surfactant is or comprises an alkyl trimethylammonium bromide, such as $C_{16}TAB$.

In embodiments wherein the source is a silica source, it may be any hydrolyzable silica source known in the art. In a preferred embodiment, the hydrolyzable silica source is or comprises an alkyl orthosilicate, such as TEOS and TMOS.

In certain embodiments, the method further includes the step of dispersing the product of step (iv) in and/or on a substrate, such as that hereinbefore described.

Suitably, the silica nanoparticle of this aspect is that hereinbefore described.

Throughout the specification the aim has been to describe the preferred embodiments of the invention without limiting the invention to any one embodiment or specific collection of features. It will therefore be appreciated by those of skill in the art that, in light of the instant disclosure, various modifications and changes can be made in the particular embodiments exemplified without departing from the scope of the present invention.

All computer programs, algorithms, patent and scientific literature referred to herein is incorporated herein by reference.

Any reference to publications cited in this specification is not an admission that the disclosures constitute common general knowledge in Australia.

In order that the invention may be more readily understood and put into practice, one or more preferred embodiments thereof will now be described, by way of example only.

EXAMPLES

Example 1

In this example the development of an ultrasensitive ELISA with 2000 times enhancement of sensitivity (ELISA+) by signal amplification is demonstrated through use of a carefully designed mesoporous silica nanoparticle (DMSN). DMSN's with easily accessible dendritic pore channels (see FIG. 1) were applied as the enzyme loading matrix to detect ultra-low concentration insulin with following advantages: (1) ultra-high enzyme loading is achieved by utilizing the DMSN with large surface area (484 $m^2\ g^{-1}$), high pore volume (1.39 $cm^3\ g^{-1}$) and large pore size (14.5 nm) to load HRP. (2) The large and open dendritic channels allow easily accessible space for substrate molecules to react with enzymes, which attributes to the ultra-high activity. (3) With the ultra-high HRP loading and easily accessible pore channels, a 2000 times enhancement of the insulin detection sensitivity in serum is achieved compared to the commercial ELISA kit tested.

Materials and Methods

Chemicals

Cetyltrimethylammonium chloride (CTAC) solution (25 wt % in $H_2O$), tetraethylorthosilicate (TEOS), triethanolamine (TEA), 3-aminopropyltriethoxysilane (APTES), phosphate buffered saline (PBS), glutaraldehyde (50 wt % in $H_2O$), cyclohexane, chlorobenzene, horseradish peroxidase (HRP) and toluene were purchased from Sigma-Aldrich. Guinea pig polyclonal to insulin ($2^{nd}$ antibody) was ordered from Abcam Australia Pty Ltd. Human insulin ELISA kit was purchased from Life Technologies (Australia Pty Ltd). All chemicals were used as received without purification. Deionized water (DI water) (18.2 mV cm) used for all experiments was obtained from a Milli-Q system (Millipore, Bedford, Mass.).

Materials Synthesis

Synthesis of DMSN-1 [15]: In a 100 mL round bottom flask, 24 mL of CTAC solution (25 wt %), 0.18 g of TEA and 36 mL of water were mixed and stirred at 60° C. for 1 h. Then, 4 mL of TEOS and 16 mL of cyclohexane (20 v/v %) were mixed and added to the solution. The solution was kept at 60° C. under a stirring speed of 150 rpm (12 h). The products were obtained after calcination at 550° C. for 5 h.

Synthesis of DMSN-2&3 [16]: In a typical synthesis, 4.8 mL CTAC (25% water solution), 0.04 g TEA and 7.2 mL Milli-Q water were mixed to form the water phase and stirred at 60° C. for 1 h. Then 4 mL of premixed oil phase (containing 3.5 mL chlorobenzene and 0.5 mL TEOS) was added to the bottom of water phase. The mixture was stirred at 60° C. under a stirring speed of 150 RPM (12 h) and 500 RPM (12 h) for the synthesis of MSN-2 and MSN-3, respectively. The solid samples were centrifuged at 15 000 RPM for 15 min and washed with ethanol for three times. In the final step, the products were obtained after calcination at 550° C. for 5 h.

Materials Characterization

Nitrogen-sorption isotherms of the samples were obtained by a Micromeritics Tristar II 3020 system at 77 K. Before the measurements, the bare/amino modified samples were degassed at 100/80° C. for at least 8 h in vacuum. The pore size distributions were calculated by the Barrett-Joyner-Halenda (BJH) method for DMSN-2&3 and the density functional theory (DFT) method for DMSN-1[15]. The total pore volume and surface area were calculated by using typical Brunauer-Emmett-Teller(BET) method. TEM images were directly taken with a JEOL 1010 microscope operated at 100 kV by dispersing the samples on a Cu grid covered with carbon films. The SEM images were obtained using JEOL JSM 7800 field-emission scanning electron microscope (FE-SEM) operated at 1 kV using gentle bean mode. The sample was dispersed in ethanol and then dropped to an aluminum foil piece and attached to the conductive carbon tape. Next, the sample was dried in vaccum over at 60° C. for 12 hours. ζ potential measurements were carried out at 25° C. using a Zetasizer Nano-ZS from Malvern Instruments. UV-vis transmittance spectra were measured with a Shimadzu UV-2450 double beam spectrophotometer. The absorbance of HRP and anti-insulin are at 401 and 278 nm, respectively.

Amino Modification of DMSN 1 g of DMSNs were dispersed in 30 mL of APTES (4 mmol) toluene solution, and refluxed at 110° C. for 18 h. The products were collected by centrifugation and washed with ethanol for 3 times. The powder was dried at room temperature overnight.

Immobilization of HRP and 2$^{nd}$ Antibody

The HRP immobilization method was modified from previous literature [7, 14]: 2 mg of DMSNs was suspended in 1 mL of PBS buffer (pH 7.4), then 1 mL of 2.5% glutaraldehyde was added and the mixture was stirred for 1 h in room temperature. The mixture was centrifuged and washed 3 times with PBS to remove the excess reagent. In the next step, the precipitate was resuspended with PBS and 2 mg of HRP was added. After stirring for 23 h, the solution was centrifuged and the precipitate was washed to remove unbound HRP. All the supernatants were collected for UV test to measure the HRP concentration. The resulting samples were named as DMSN-1-H, DMSN-2-H and DMSN-3-H.

The 2$^{nd}$ antibody immobilization method was modified from previous literature [7, 14]: After immobilized with HRP for 6 h, 1 mL of 0.2 mg/mL anti-insulin was added into the solution and further stirring for 17 h. The products were centrifuged and washed to remove unbound HRP and anti-insulin. All the supernatants were collected for UV test to measure the levels of HRP and anti-insulin. The resulting samples were named as DMSN-1-H-A, DMSN-2-H-A and DMSN-3-H-A.

The Activity Measurement of Immobilized HRP

The activity measurement of immobilized HRP was conducted by using TMB/H$_2$O$_2$ as substrates, and the results were compared with free HRP. DMSNs-H solution was prepared in PBS with a different HRP concentration (0-0.25 µg mL$^{-1}$). Then, they were mixed with TMB/H$_2$O$_2$ (give a total volume of 50 µL) in a 96-well microplate and incubated at 25° C. for 10 min. Then, 50 µL of 1 M HCl was added to stop the reaction. The optical density (O.D.) was read at 450 nm by a microplate reader.

Ultrasensitive ELISA

The standard insulin solutions with ultra-low concentrations (1~1/2000 times of LOD of commercial ELISA kit=6.86~3.43×10$^{-3}$ pg mL$^{-1}$) were prepared freshly. They were stepwise diluted from the standard solution in the ELISA kit (containing 168 pg mL$^{-1}$ of insulin in human serum).

ELISA$^+$ was conducted following the instruction of traditional ELISA kit by simply replacing the anti-insulin HRP with functionalized DMSNs-H-A. Typically, 50 µL of each standards/control/samples was added into the wells together with 50 µL of anti-insulin HRP, incubating for 30 min at room temperature. For the ELISA$^+$, 50 µL (4 µg mL$^{-1}$) of functionalized DMSNs-H-A were employed to replace the anti-insulin HRP. The liquid was decanted thoroughly and the wells were washed 4 times with the diluted wash solution before adding 100 µL stabilized chromogen. After 15 min, 100 µL of stop solution (1 M HCl) was added and the plate was measured by reading the absorbance at 450 nm using a Synergy HT microplate reader within 1 h. For the control experiments, PBS was used to replace insulin contained serum as a negative control. All the standards/control/samples were run in duplicate.

The standard curve of ELISA$^+$ was built by using the above procedure to test a series of insulin samples in low concentrations (20-100 fg ml$^{-1}$). To test the recovery rate, 1 µl of insulin (1 fg) was spiked to 50 µl (3 fg) of insulin standard solution, and it became sample x with 4 fg of insulin theoretically. Then, sample x was tested by ELISA$^+$ and calculated according to the standard curve. The recovery rate is the difference between calculated value and theoratical value (4 fg). Samples were run in duplicate.

Results and Discussion

Synthesis and Characterization of DMSNs

Figure 2:
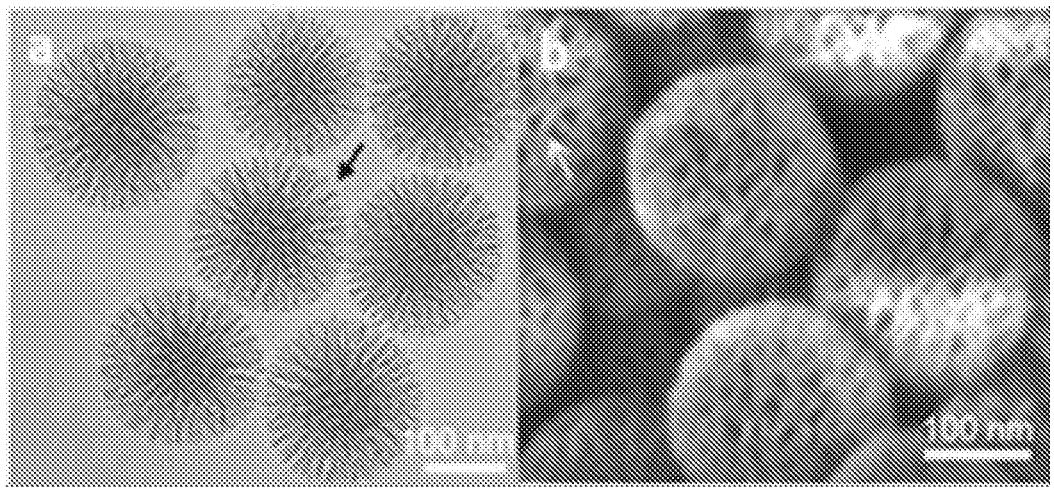
FIG. 2. (a) The transmission electron microscopy (TEM) and (b) Scanning electron microscopy (SEM) images of DMSN-2. The arrows show the open pore channels.
Figure 7:
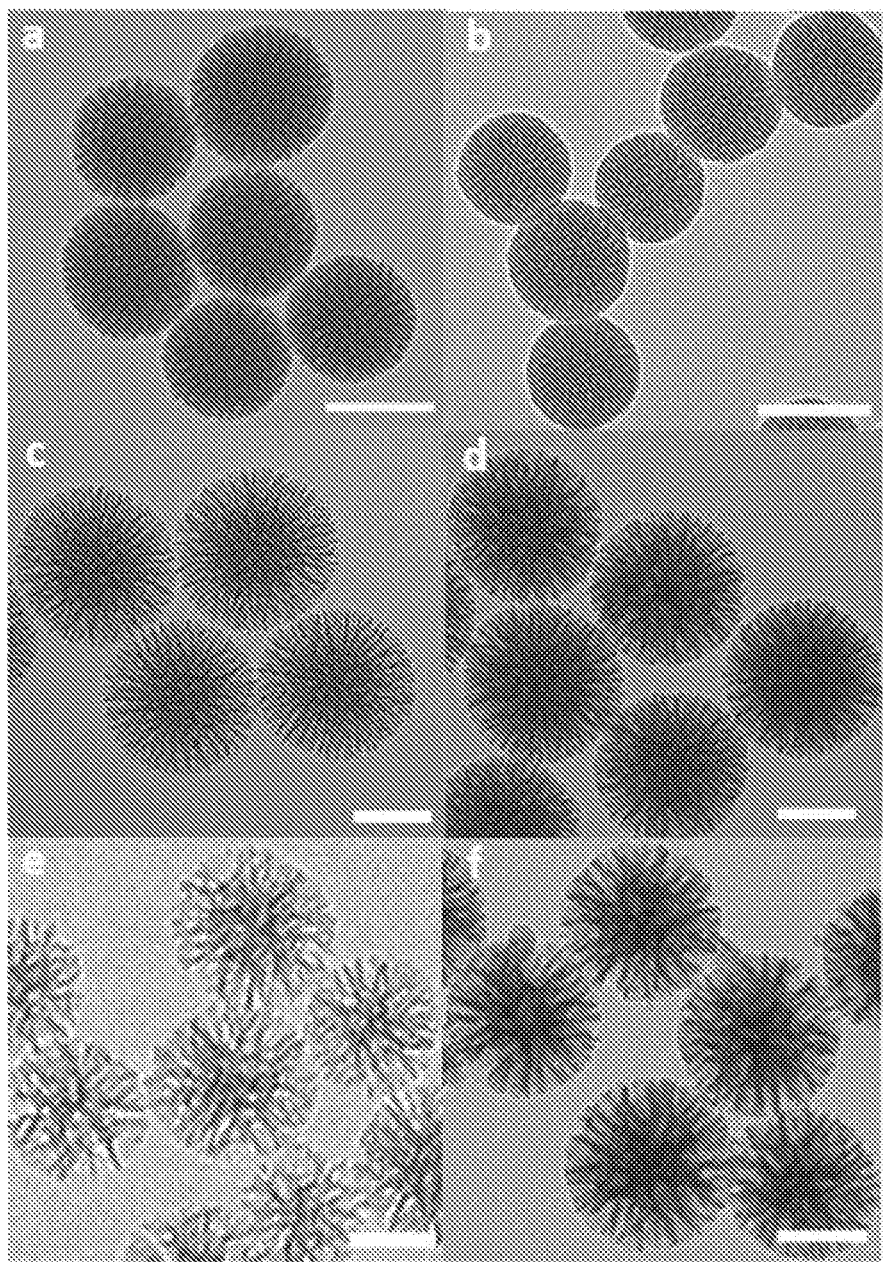
FIG. 7. TEM images of (a) DMSN-1, (c) DMSN-2, (e) DMSN-3; and amino modified (b) DMSN-1-$NH_2$, (d) DMSN-2-$NH_2$, (f) DMSN-3-$NH_2$. Scale bar: 100 nm.

To investigate the pore size effect on HRP loading and ELISA$^+$ sensitivity, three MSNs with similar structure but different pore sizes were selected [15, 16]. With the pore size increase, three MSNs were denoted as DMSN-1 (6.9 nm), DMSN-2 (16 nm) and DMSN-3 (40 nm). Amino modification was conducted to graft —NH$_2$ in DMSNs for HRP immobilization (Scheme S1 in the ESM), showing that the mesostructures of three DMSNs are maintained after functionalization. TEM and SEM are used to characterize the structures of DMSNs. The TEM images in FIG. 7 display the spherical structure and pore channels of DMSNs before (FIG. 7 (a, c, e) and after (FIG. 7 (b, d, f)) amino modification. Specially, the open pore channels of DMSN-2 are revealed by TEM and SEM images in FIG. 2.

Figure 8:
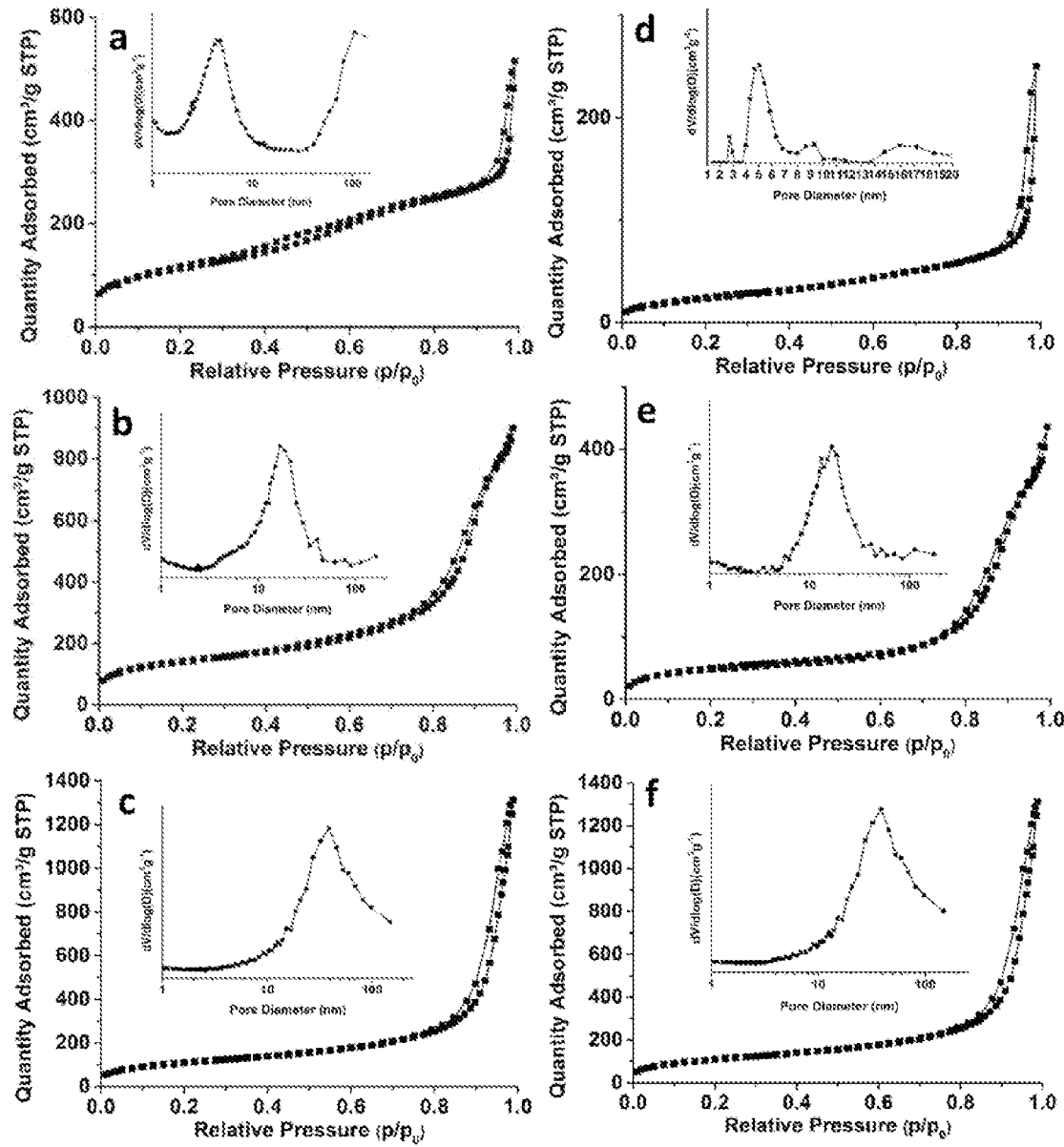
FIG. 8. Nitrogen adsorption-desorption isotherms and pore size distributions of (a) DMSN-1, (b) DMSN-2, (c) DMSN-3 and amino modified (d) DMSN-1-$NH_2$, (e) DMSN-2-$NH_2$, (f) DMSN-3-$NH_2$.

Nitrogen adsorption was conducted to assess the pore sizes of DMSNs. The adsorption-desorption plots exhibit type IV isotherms for all the DMSNs (FIG. 8). The pore size distributions were calculated by the density functional theory (DFT) method for DMSN-1[15] and Barrett-Joyner-Halenda (BJH) method for MSN-2&3. The amino modified MSN-1&2 have reduced pore sizes when compared with pristine ones (DMSN-1: 6.9 to 4.9 nm; DMSN-2: 16 to 14.5 nm), while no significant decrease can be observed in DMSN-3. Similarly, the total pore volume and surface area calculated by typical Brunauer-Emmett-Teller (BET) method are decreased after amino modification for all the DMSNs (Table 1), but the less reductions were observed for DMSN-3-NH$_2$ compare to the other two. The decreases of pore size/pore volume/surface area are due to the occupation of inner pore surface by amino groups, and the tendency is more obvious for small pore materials which is in agreement with previous reports[17, 18].

The different pore sizes of DMSN-1 (4.9 nm), DMSN-2 (14.5 nm) and DMSN-3 (40 nm) allow the investigation of pore size effect on HRP/2$^{nd}$ antibody loading and eventually on ELISA sensitivity. Among three, DMSN-2 with a pore size larger than HRP but smaller than 2$^{nd}$ antibody is expected to have best performance as it enables the availability of mesopores for HRP loading while limits the 2$^{nd}$ antibody on outer surface for antigen-antibody binding. ζ potential measurement shows that the charge for original DMSN-1/2/3 are −25, −18.4 and −27.3, while for amino modified DMSN-1/2/3-NH$_2$ are 36, 14 and 26, respectively. The charge changed from negative to positive, indicating success of the amino modification (Table 1).

Immobilization of HRP

Figure 6:
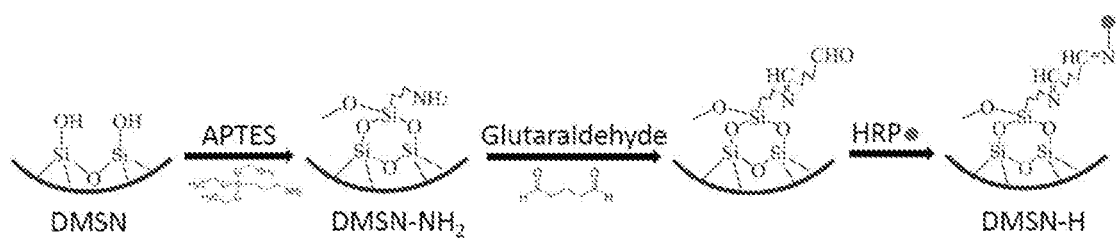
FIG. 6. Illustration showing the mechanism of HRP immobilization.

The immobilization of HRP was conducted through the covalent binding using the well-developed method as shown in FIG. 6, and glutaraldehyde was employed as the binding agent. The covalent binding would avoid the leakage of HRP during the ELISA process, which may lead to reduced sensitivity. The resulting materials were named as DMSN-1-H, DMSN-2-H and DMSN-3-H with loading amounts of 283, 390 and 382 mg g$^{-1}$, respectively. Compare to DMSN-2 (390 mg g$^{-1}$), the pore size of DMSN-1 (4.9 nm, with NH$_2$ modification) is slightly smaller than HRP (6*5*4 nm), which reduces the possibility of HRP entering the mesopores, thus the loading amount is less (283 mg g$^{-1}$). The high surface area & pore volume of amino modified DMSN-3 give a high loading capacity, but the very large pore size (40 nm) has little entrapping effect on HRP, thus the synergistic effect results in a HRP loading amount of 382 mg g$^{-1}$, which is similar to that of DMSN-2 with a smaller surface area & pore volume (390 mg g$^{-1}$).

Activity Test of HRP

Figure 3:
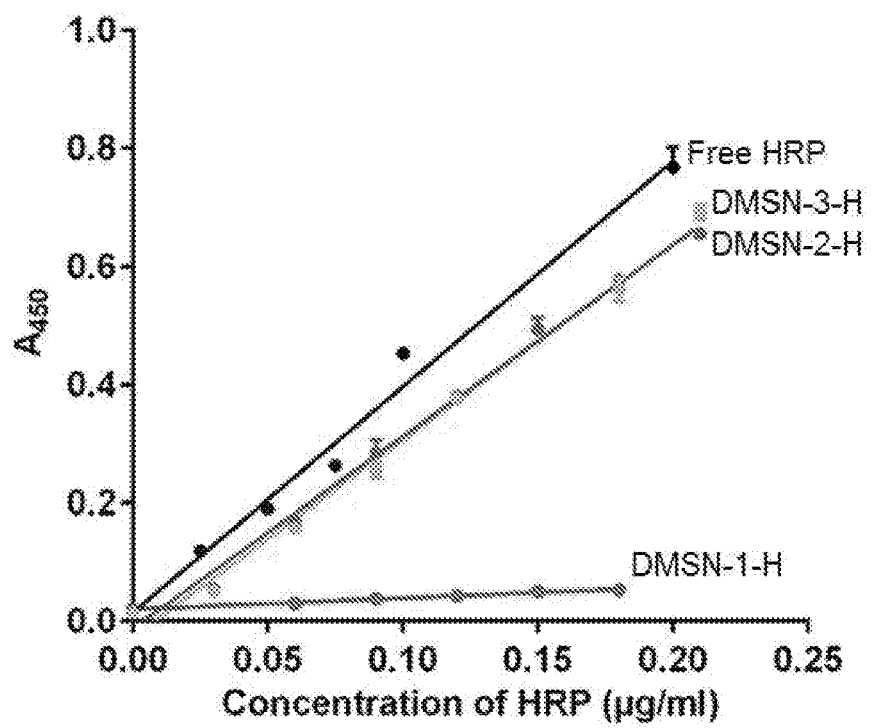
FIG. 3. Activity of immobilized HRP relative to free HRP measured by end-point method using $TMB/H_2O_2$ as substrates. The results were normalized to concentration of HRP.

To know the activity of immobilized HRP, its catalytic property was compared with free HRP. FIG. 3 illustrates the linear relationship between HRP concentration and optical density at 450 nm ($A_{450}$). The activities of DMSNs-H calculated from the slopes of each linear regression curve are 5%, 87% and 85% for DMSN-1-H, DMSN-2-H and DMSN-3-H. The ultra-low HRP activity in MSN-1 may result from the limit reaction between loaded HRP and substrate, which is confined by the small mesopores with similar size as HRP. 87% and 85% of catalytic property in DMSN-2-H and DMSN-3-H suggests large pore size with easily accessible pore channels is beneficial to high enzyme activity.

Immobilization of 2$^{nd}$ Antibody

After ensuring the enzyme activity of immobilized HRP can be largely maintained, DMSNs with both HRP and 2$^{nd}$ anti-insulin antibody (denote DMSN-1-H-A, DMSN-2-H-A and DMSN-3-H-A) were developed as labels for ultra-sensitive ELISA$^+$. The immobilization of 2$^{nd}$ antibody was conducted after the loading of HRP and utilize the remaining —CHO group on DMSNs for covalent binding, the process is similar to that of HRP loading (Scheme S1). The loading amounts of HRP in this condition are similar as above. 57, 60, 55 mg g$^{-1}$ (Table 3) of 2$^{nd}$ antibody were conjugated on DMSN-1, DMSN-2 and DMSN-3, respectively. No significant difference between DMSNs on the loading amount of 2$^{nd}$ antibody is observed, which may due to the small feeding ratio (100 mg antibody: 1 g DMSN).

Sensitive Detection of Insulin in Serum Using ELISA$^+$

The functional DMSNs with both HRP and 2$^{nd}$ antibody were applied for ultra-sensitive insulin detection in human serum. All the insulin samples (in the range of 3.85 fg ml$^{-1}$-7.7 pg ml$^{-1}$) are freshly prepared by diluting the standard solution of a commercial ELISA kit, which has a detection limit (LOD$_C$) of 7.7 pg ml$^{-1}$ as suggested in the instruction. When using DMSN-2-H-A and DMSN-3-H-A to amplify the colour signal (FIG. 4), the detection limit decreased to 3.85 fg ml$^{-1}$, which is equal to 1/2000 of LOD$_C$. Although DMSN-2-H-A and DMSN-3-H-A have the same detection limit, but the former gives higher OD intensities thus it is the best signal amplified candidate among three DMSNs. Meanwhile, the lowest detectable concentration of DMSN-1-H-A is 7.7 fg ml$^{-1}$ (1/1000 of LOD$_C$), which is higher than that of the other two DMSNs. It is due to the less loading and low activity of HRP.

Compared with commercial ELISA kit, ELISA$^+$ shows a 2000 times enhancement of detection sensitivity. It is achieved by the high activity and high colour reaction efficacy of enzyme in DMSN-2, which with suitable pore size and open pore channels. In addition, the distribution of the 2$^{nd}$ antibody plays an important role for the high sensitivity as well. In the cases of DMSN-1 and DMSN-2, the large size of 2$^{nd}$ antibody (~20 nm) limits their location on the outer surface. Whereas the large pore size of DMSN-3 (40 nm) would allow the loading of 2$^{nd}$ antibody inside the pores, which hinders the binding of 2$^{nd}$ antibody with antigen (insulin), that is the possible reason of the less sensitivity of DMSN-3-H-A compared to DMSN-2-H-A.

Figure 4:
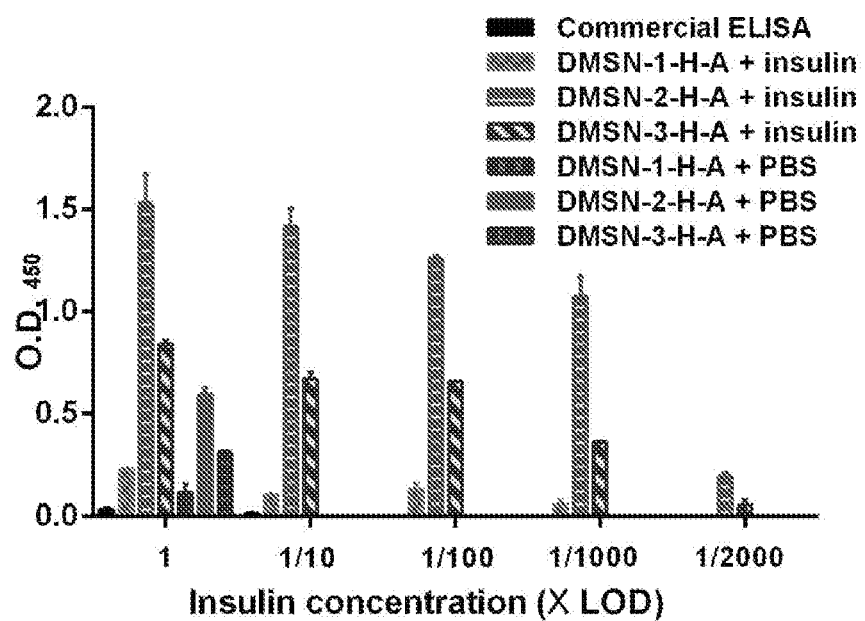
FIG. 4. OD value of commercial ELISA and ELISA based on DMSNs at different insulin concentration. The numbers (1, 1/10, 1/100, 1/1000 and 1/2000) on x axis represent the insulin dilution times of LODC (detection limit of commercial ELISA kit). Control groups with only DMSNs-H-A and no insulin addition were included and the values of DMSN-1-H-A, DMSN-2-H-A and DMSN-3-H-A are shown as pink, green and purple bars respectively in the 1 LOD concentration group.

Considering there may be some free nanoparticles (DMSNs-H-A) stick on the wells after washing process, which may produce some colour as well, control groups with only DMSNs-H-A (FIG. 4) were set to evaluate the colour signal from left DMSNs-H-A. Standard procedure with all the incubation and washing steps was applied to the control groups, but with no insulin (antigen) added. The mean signal intensities from each stuck DMSNs-H-A (control groups) are 0.115, 0.594 and 0.314 for DMSN-1-H-A, DMSN-2-H-A and DMSN-3-H-A, which are revealed in FIG. 4 under the concentration 1 area. Thus, the intensity value of each experimental group showed in FIG. 4 representing the absolute colour change calculated by the detected value minus the value of corresponding control.

Figure 5:
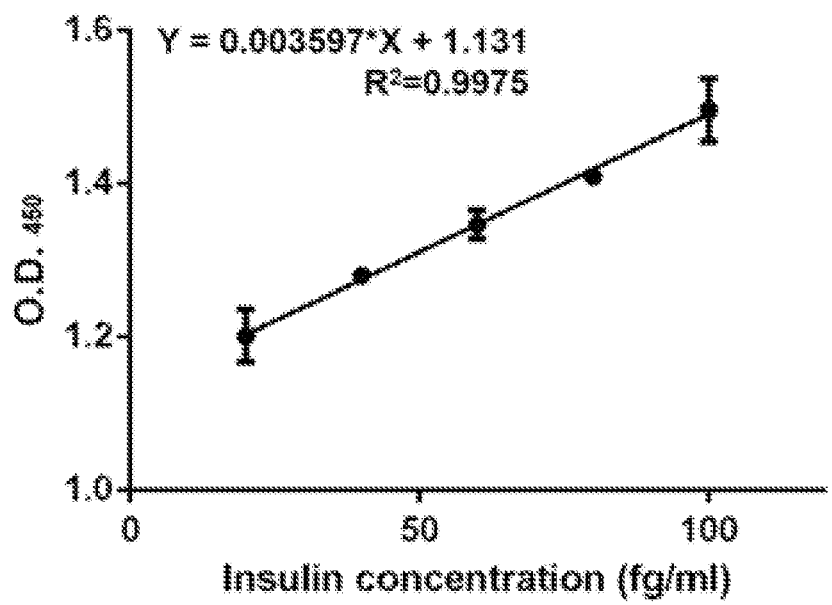
FIG. 5. Standard curves showing the quantification range of ELISA+.

A calibration curve was built to confirm the quantification ability of ELISA$^+$ by testing a series of insulin samples in low concentrations (20-100 fg ml$^{-1}$). The curve is shown in FIG. 5 with a linear regression coefficient ($R^2$) of 0.9975, which suggests the ELISA$^+$ is highly reliable for human insulin quantification. When compare to the commercial kit with a quantification limit of 7.7 pg ml$^{-1}$, the ELISA$^+$ shows an extremely high sensitivity. To further confirm the quantification efficacy of ELISA$^+$, a recovery rate was measured by spiking 1 μl of 1 pg ml$^{-1}$ insulin to a standard solution. The recovery rate of ELISA$^+$ is 81%, which is comparable to the previous reports.[19, 20] In a study, ICP-MS was employed for the detection of insulin in the concentration of 111 pM (640 pg ml$^{-1}$) and a recovery rate of 91% is achieved[20]. Another report used liquid chromatography for low abundance (121 pg ml$^{-1}$) human insulin detection, but the recovery rate is only 33.2%-51.7% [19]. The high recovery rate of the addition with tiny volume (1 μl) ensures the sensitive detection of precious samples with trace amount or limit volume.

Conclusions

An ultrasensitive ELISA$^+$ is successfully developed by using DMSN with high HRP loading and easily accessible dendritic pore channels for the colour signal amplification. A 2000 times enhancement of detection sensitivity in serum is achieved compare to commercial ELISA kit. This study proposes a great idea to improve ELISA efficiency by using DMSN for colour amplification. Moreover, the ELISA$^+$ can be widely used for the ultrasensitive detection of other proteins. Furthermore, it is highly possible to couple ELISA$^+$ with current techniques to achieve super-performance.

In addition to the above, the DMSNs that were developed demonstrate a large and open pore structure that may facilitate easy loading of quantum dots thereon and appropriately unrestricted arrangement on the walls of the pores so as to minimize quenching of any emitted light therefrom.

TABLE 1

Surface area, pore volume, pore size and ζ potential of materials

| Sample | BET surface area (m$^2$/g) | Pore volume (cm$^3$/g) | BJH pore size (nm) | ζ potential |
|---|---|---|---|---|
| DMSN-1 | 396 | 0.80 | 6.9 (DFT)* | −25 |
| DMSN-1-NH$_2$ | 91 | 0.39 | 4.9 (DFT)* | 36 |
| DMSN-2 | 484 | 1.39 | 16 | −18.4 |
| DMSN-2-NH$_2$ | 176 | 0.67 | 14.5 | 14 |
| DMSN-3 | 389 | 2.03 | 40 | −27.3 |
| DMSN-3-NH$_2$ | 323 | 1.65 | 40 | 26 |

*DFT method was applied for the pore size measurement.[15]

TABLE 2

HRP loading of materials

|  | DMSN-1 | DMSN-2 | DMSN-3 |
|---|---|---|---|
| Loading Amount (mg g$^{-1}$) | 283 ± 10 | 390 ± 9 | 382 ± 15 |

TABLE 3

2$^{nd}$ antibody loading of materials

|  | DMSN-1 | DMSN-2 | DMSN-3 |
|---|---|---|---|
| Loading Amount (mg g$^{-1}$) | 57 ± 5 | 60 ± 4 | 55 ± 4 |

Example 2

Synthesis of Thiol-Modified Dendritic Silica Particles Materials and Methods: (Thiols)

Chemicals: Tetraethyl orthosilicate (TEOS), triethanolamine (TEA), (3-Mercaptopropyl) trimethoxysilane (MPTMS), sodium salicylate, cetyltrimethylammonium bromide (CTAB), ethanol and hydrochloric acid (37% wt) were purchased from Sigma-Aldrich. Doubly distilled water obtained from a laboratory purification system was used throughout the experiments. In all experiments, water was deoxygenated in ultrasonic bath and then by bubbling $N_2$ gas for 10 min before use.

Synthesis of T-MSN. In a typical synthesis, TEA (68 mg) was dissolved in distilled water (25 mL) at 80° C. under intensive stirring for 30 min. After addition of CTAB (380 mg) and sodium salicylate (84 mg), the resulting mixture was stirred for 1 h and then TEOS (3.8 ml) was added. After further stirring at 80° C. for 30 min, MPTMS (0.1625 ml) was added to the reaction solution. The product was collected by centrifugation after 6 h, washed several times with ethanol to remove the residual reactants and subsequently extracted three times at 60° C. for 6 h with a solution of hydrochloric acid in ethanol at room temperature to remove the template CTAB. The final product, denoted as T-MSN, was dispersed in water (30 ml).

Figure 9:
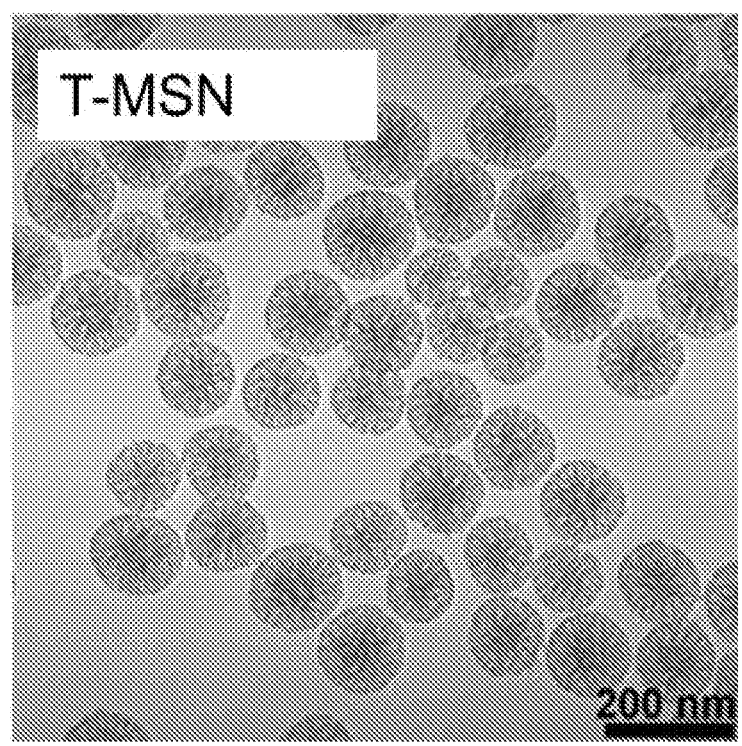
FIG. 9. TEM micrographs showing silica nanoparticles incorporating thiol anchoring groups where the silica nanoparticle has a radial dendritic structure with silica spikes radiating out from the core.

Results. The particles produced by the above synthesis had a dendritic structure with spikes emanating radially out from a central core as shown in FIG. 9. The average particle diameter as measured by TEM was found to be 145 nm while average particle size measured by dynamic light scattering (DLS, Zetasizer) was found to be slightly higher at 164 nm. Nitrogen sorption analysis showed an average pore size of 14.3 nm and a BET surface area of 528 m$^2$/g. The sulfur content was determined to be 5.97 wt. % measured using a CHNS elemental analyser.

Example 3

Loading Quantum Dots Into Thiol-Modified Particles

CdSe quantum dots with 4 nm diameter were dispersed in 1 mL of CHCl$_3$ at a concentration of 10 mg/mL. To this was added a dispersion of the T-MSN particles synthesized at Example 2 (1 mg in 1 mL ethanol). The T-MSN particles were shaken with the quantum dots for a few minutes and the resulting mixture was centrifuged and washed with EtOH several times. The quantum dots were successfully loaded into the T-MSN particles with the loading amount of 0.6 g of quantum dots per gram of T-MSN.

Example 4

An Alternative Method of Silica Nanoparticle Synthesis

Method. In this example, monodisperse mesoporous silica nanoparticles were synthesized via a one-pot, surfactant-free process by way of the Stöber synthesis condition. Typically, an aqueous-alcoholic solution was prepared by mixing ethanol (40 mL), distilled water (10 mL), ammonium hydroxide (1.56 mL) and ethylenediamine solution (EDA, 0.225 mL) under stirring. After that, 3-aminophenol (0.412 g), formaldehyde solution (0.9 mL), TEOS (1.56 mL) were added to the above-mentioned solution. Then the mixture was vigorously stirred for 5 h. The as synthesized composite was collected by centrifugation, ethanol washing and drying. Finally, monodisperse mesoporous silica nanoparticles were harvested after calcination in air.

Figure 11:
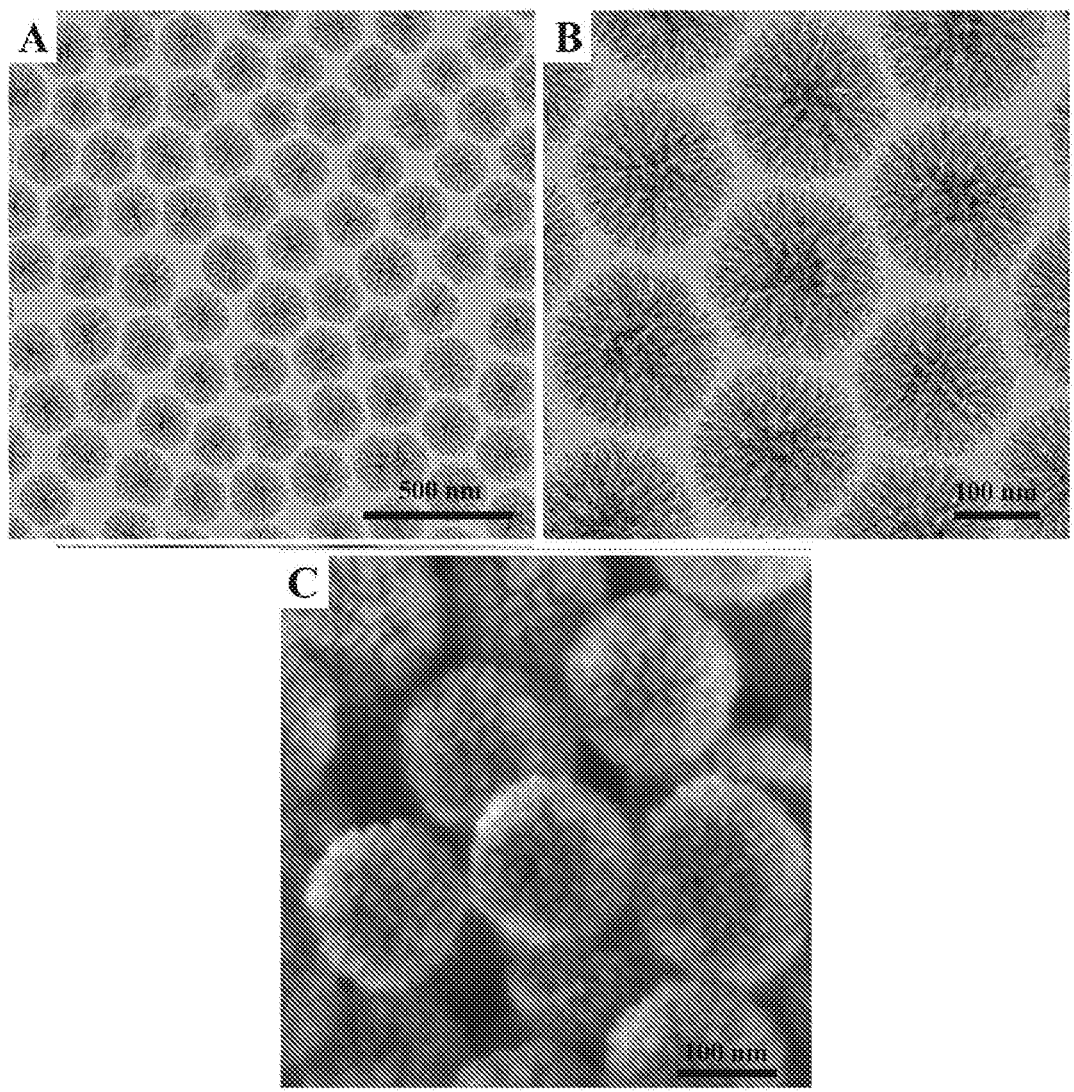
FIG. 11. TEM images (A-B), SEM image (C), $N_2$ adsorption/desorption isotherms (D) and the corresponding pore size distributions (inset) of the monodisperse mesoporous silica nanoparticles of Example 4.
Figure 11:
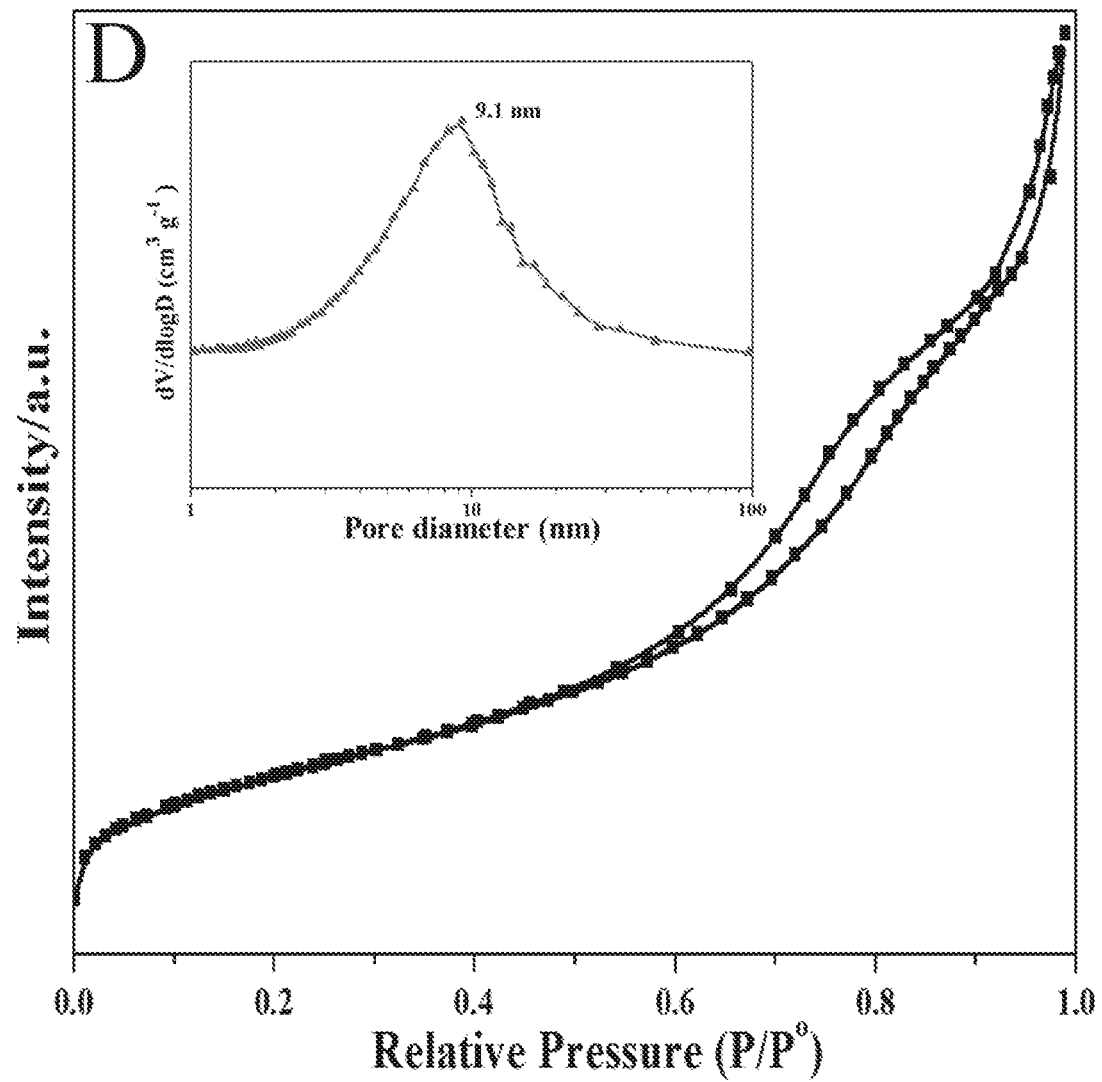

Characterization. TEM images (FIG. 11A) show that the well-dispersed silica nanoparticles with a uniform morphology are obtained. As shown in FIG. 11B, it is clear that the mean particle diameter is appropriately 180±5 nm and the particles exhibit nanosized radial spikes. SEM image (FIG. 11C) further shows the uniform size silica nanoparticles with a dense distribution of silica spikes. The nitrogen adsorption and desorption isotherm (FIG. 11D) shows a typical type IV isotherm with distinct hysteresis loops, which indicates the existence of a high degree of mesoporosity. The corresponding Barrett-Joyner-Halenda (BJH) pore size distribution curve (FIG. 11D, the inset curve) derived from the adsorption branch exhibits a relatively broad peak centered at 9.1 nm.

REFERENCES

[1] Crowther, J. R., *The ELISA guidebook*. 2000; p 1-413.
[2] Singh, A. K.; Kilpatrick, P. K.; Carbonell, R. G., Noncompetitive Immunoassays Using Bifunctional Unilamellar Vesicles or Liposomes. *Biotechnol Progr* 1995, 11, 333-341.
[3] Mani, V.; Chikkaveeraiah, B. V.; Patel, V.; Gutkind, J. S.; Rusling, J. F., Ultrasensitive Immunosensor for Cancer Biomarker Proteins Using Gold Nanoparticle Film Electrodes and Multienzyme-Particle Amplification. *Acs Nano* 2009, 3, 585-594.
[4] Zhang, Z. X.; Liu, Y.; Zhang, C. Y.; Luan, W. X., Horseradish peroxidase and antibody labeled gold nanoparticle probe for amplified immunoassay of ciguatoxin in fish samples based on capillary electrophoresis with electrochemical detection. *Toxicon* 2015, 96, 89-95.
[5] Qu, Z. Y.; Xu, H.; Xu, P.; Chen, K. M.; Mu, R.; Fu, J. P.; Gu, H. C., Ultrasensitive ELISA Using Enzyme-Loaded Nanospherical Brushes as Labels. *Anal Chem* 2014, 86, 9367-9371.
[6] Dhawan, S., Design and construction of novel molecular conjugates for signal amplification (II): use of multivalent polystyrene microparticles and lysine peptide chains to generate immunoglobulinhorseradish peroxidase conjugates. *Peptides* 2002, 23, 2099-2110.
[7] Yang, M. H.; Li, H.; Javadi, A.; Gong, S. Q., Multifunctional mesoporous silica nanoparticles as labels for the preparation of ultrasensitive electrochemical immunosensors. *Biomaterials* 2010, 31, 3281-3286.

[8] Wu, Y. F.; Xue, P.; Kang, Y. J.; Hui, K. M., Paper-Based Microfluidic Electrochemical Immunodevice Integrated with Nanobioprobes onto Graphene Film for Ultrasensitive Multiplexed Detection of Cancer Biomarkers. *Anal Chem* 2013, 85, 8661-8668.

[9] Rodrigues, R. C.; Ortiz, C.; Berenguer-Murcia, A.; Torres, R.; Fernandez-Lafuente, R., Modifying enzyme activity and selectivity by immobilization. *Chem Soc Rev* 2013, 42, 6290-6307.

[10] Takahashi, H.; Li, B.; Sasaki, T.; Miyazaki, C.; Kajino, T.; Inagaki, S., Catalytic activity in organic solvents and stability of immobilized enzymes depend on the pore size and surface characteristics of mesoporous silica. *Chem Mater* 2000, 12, 3301-3305.

[11] Lin, N.; Gao, L.; Chen, Z.; Zhu, J. H., Elevating enzyme activity through the immobilization of horseradish peroxidase onto periodic mesoporous organosilicas. *New J Chem* 2011, 35, 1867-1875.

[12] Slowing, I. I.; Vivero-Escoto, J. L.; Wu, C. W.; Lin, V. S. Y., Mesoporous silica nanoparticles as controlled release drug delivery and gene transfection carriers. *Adv Drug Deliver Rev* 2008, 60, 1278-1288.

[13] Vallet-Regi, M.; Colilla, M.; Gonzalez, B., Medical applications of organic-inorganic hybrid materials within the field of silica-based bioceramics. *Chem Soc Rev* 2011, 40, 596-607.

[14] Chen, L. L.; Zhang, Z. J.; Zhang, P.; Zhang, X. M.; Fu, A. H., An ultra-sensitive chemiluminescence immunosensor of carcinoembryonic antigen using HRP-functionalized mesoporous silica nanoparticles as labels. *Sensor Actuat B-Chem* 2011, 155, 557-561.

[15] Shen, D. K.; Yang, J. P.; Li, X. M.; Zhou, L.; Zhang, R. Y.; Li, W.; Chen, L.; Wang, R.; Zhang, F.; Zhao, D. Y., Biphase Stratification Approach to Three-Dimensional Dendritic Biodegradable Mesoporous Silica Nanospheres. *Nano Lett* 2014, 14, 923-932.

[16] Xu, C.; Yu, M.; Noonan, O.; Zhang, J.; Song, H.; Zhang, H.; Lei, C.; Niu, Y.; Huang, X.; Yang, Y.; Yu, C., Core-Cone Structured Monodispersed Mesoporous Silica Nanoparticles with Ultra-large Cavity for Protein Delivery. 2015, 11, 5949-5955.

[17] Walcarius, A.; Etienne, M.; Lebeau, B., Rate of access to the binding sites in organically modified silicates. 2. Ordered mesoporous silicas grafted with amine or thiol groups. *Chem Mater* 2003, 15, 2161-2173.

[18] Burleigh, M. C.; Markowitz, M. A.; Spector, M. S.; Gaber, B. P., Amine-functionalized periodic mesoporous organosilicas. *Chem Mater* 2001, 13, 4760-4766.

[19] Hess, C.; Thomas, A.; Thevis, M.; Stratmann, B.; Quester, W.; Tschoepe, D.; Madea, B.; Musshoff, F., Simultaneous determination and validated quantification of human insulin and its synthetic analogues in human blood serum by immunoaffinity purification and liquid chromatography-mass spectrometry. *Anal Bioanal Chem* 2012, 404, 1813-1822.

[20] Liu, J. M.; Yan, X. P., Ultrasensitive, selective and simultaneous detection of cytochrome c and insulin based on immunoassay and aptamer-based bioassay in combination with Au/Ag nanoparticle tagging and ICP-MS detection. *J Anal Atom Spectrom* 2011, 26, 1191-1197.

The invention claimed is:

1. A method for detecting an analyte in a sample, including a step of contacting said analyte with a nanoparticle to facilitate binding thereto, wherein the nanoparticle comprises:
   (i) a core;
   (ii) pores extending radially from said core and being defined by spaces between an array of dendritic spikes radiating outwardly from a surface of the core, wherein the pores have an average pore size of between about 10 nm and about 20 nm;
   (iii) a binding agent for binding the analyte; and
   (iv) a detection agent immobilized within said pores;
to thereby detect said analyte.

2. The method of claim 1, wherein the nanoparticle is a silica nanoparticle.

3. The method of claim 1, wherein the pores are substantially conical.

4. The method of claim 1, wherein the nanoparticle has an average particle size of between about 50 nm and about 250 nm.

5. The method of claim 1, further including a step of producing a reporter signal from the detection agent.

6. The method of claim 5, further including a step of detecting the reporter signal.

* * * * *

UNITED STATES PATENT AND TRADEMARK OFFICE
CERTIFICATE OF CORRECTION

PATENT NO. : 11,867,699 B2
APPLICATION NO. : 16/308219
DATED : January 9, 2024
INVENTOR(S) : Chengzhong Yu et al.

Page 1 of 1

It is certified that error appears in the above-identified patent and that said Letters Patent is hereby corrected as shown below:

On the Title Page

(30) Foreign Application Priority Data: Please add --Jun. 10, 2016 (AU) 2016902274--

In the Claims

Column 34, Line 21: Please change "facilitate binding thereto, wherein the nanoparticle comprises:" to --facilitate binding thereto in vitro, wherein the nanoparticle comprises:--

Column 34, Line 29: Please change "(iii) a binding agent for binding the analyte; and" to --(iii) a binding agent for binding the analyte in vitro; and--

Signed and Sealed this
Twenty-first Day of May, 2024

Katherine Kelly Vidal
*Director of the United States Patent and Trademark Office*